US009744179B2

(12) United States Patent
Griffith et al.

(10) Patent No.: US 9,744,179 B2
(45) Date of Patent: Aug. 29, 2017

(54) TETRACYCLINE COMPOSITIONS

(71) Applicant: Rempex Pharmaceuticals, Inc., San Diego, CA (US)

(72) Inventors: David C. Griffith, San Marcos, CA (US); Serge Boyer, San Diego, CA (US); Scott Hecker, Del Mar, CA (US); Michael N. Dudley, San Diego, CA (US)

(73) Assignee: Rempex Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 14/562,449

(22) Filed: Dec. 5, 2014

(65) Prior Publication Data

US 2015/0094282 A1 Apr. 2, 2015

Related U.S. Application Data

(63) Continuation of application No. 13/654,018, filed on Oct. 17, 2012, now Pat. No. 9,278,105, which is a continuation of application No. PCT/US2011/036351, filed on May 12, 2011.

(60) Provisional application No. 61/392,304, filed on Oct. 12, 2010, provisional application No. 61/334,106, filed on May 12, 2010.

(51) Int. Cl.
| | |
|---|---|
| *A01N 37/18* | (2006.01) |
| *A61K 31/65* | (2006.01) |
| *A61K 9/00* | (2006.01) |
| *A61K 47/02* | (2006.01) |

(52) U.S. Cl.
CPC ............ *A61K 31/65* (2013.01); *A61K 9/0019* (2013.01); *A61K 47/02* (2013.01)

(58) Field of Classification Search
None
See application file for complete search history.

(56) References Cited

U.S. PATENT DOCUMENTS

| | | | |
|---|---|---|---|
| 2,736,725 A | 2/1956 | Ritter | |
| 2,980,584 A | 4/1961 | Hammer | |
| 3,166,474 A | 1/1965 | Remmers et al. | |
| 3,226,436 A | 12/1965 | Petisi et al. | |
| 3,232,834 A | 2/1966 | Gordon et al. | |
| 3,275,513 A | 9/1966 | Nash et al. | |
| 3,335,055 A | 8/1967 | Weidenheimer | |
| 3,957,980 A | 5/1976 | Noseworthy | |
| 4,038,315 A | 7/1977 | Tobkes | |
| 4,060,605 A | 11/1977 | Cotti | |
| 4,086,332 A | 4/1978 | Armstrong | |
| 4,701,320 A | 10/1987 | Hasegawa et al. | |
| 5,075,295 A | 12/1991 | Zupan et al. | |
| 5,494,903 A | 2/1996 | Hlavka | |
| 6,193,994 B1 | 2/2001 | Lee et al. | |
| 6,245,735 B1 | 6/2001 | Pier | |
| 6,284,277 B1 | 9/2001 | Bouloumie et al. | |
| 6,310,053 B1 | 10/2001 | Patterson | |
| 6,375,982 B1 | 4/2002 | Cherukuri | |
| 6,406,717 B2 | 6/2002 | Cherukuri | |
| 6,589,556 B2 | 7/2003 | Cherukuri | |
| 6,825,178 B1 | 11/2004 | Pier | |
| 7,229,641 B2 | 6/2007 | Cherukuri | |
| 7,485,319 B2 | 2/2009 | deVries et al. | |
| 7,820,641 B2 | 10/2010 | Nelson et al. | |
| 7,879,828 B2* | 2/2011 | Fawzi .................. | A61K 9/0019 514/154 |
| 9,084,802 B2 | 7/2015 | Griffith et al. | |
| 9,278,105 B2 | 3/2016 | Griffith et al. | |
| 2002/0042394 A1 | 4/2002 | Hogenkamp et al. | |
| 2002/0187188 A1 | 12/2002 | Cherukuri | |
| 2003/0083318 A1 | 5/2003 | Julien et al. | |
| 2003/0171340 A1 | 9/2003 | Isbister | |
| 2004/0077601 A1 | 4/2004 | Adams et al. | |
| 2004/0131628 A1 | 7/2004 | Bratzler et al. | |
| 2004/0202725 A1 | 10/2004 | Dascalu | |
| 2004/0235801 A1 | 11/2004 | Julian et al. | |
| 2005/0019396 A1 | 1/2005 | deVries et al. | |
| 2005/0038002 A1 | 2/2005 | Nelson et al. | |
| 2005/0084490 A1 | 4/2005 | Adams et al. | |
| 2006/0141054 A1 | 6/2006 | Piccariello | |
| 2006/0183719 A1 | 8/2006 | deVries et al. | |
| 2006/0247181 A1 | 11/2006 | Fawzi et al. | |
| 2007/0243244 A1* | 10/2007 | Shah et al. .................... | 424/456 |
| 2007/0282001 A1 | 12/2007 | Chi | |
| 2008/0015352 A1 | 1/2008 | Piccariello | |

(Continued)

FOREIGN PATENT DOCUMENTS

| | | |
|---|---|---|
| BE | 905528 | 2/1987 |
| BR | 9804395 | 6/2000 |

(Continued)

OTHER PUBLICATIONS

Anonymous, Russian Website Medstream, "The antibiotic is able to treat stroke", Online Oct. 9, 2009 at http://medstream.ru/news/28775.html.; 4 pages.
Radar Medication Guide, "Omnipak (Omipaque)", last update Jul. 31, 2003; Russian website at http://www.rlsnet.ru/tn__index_id__2438.htm; 14 pages.
Pfizer Drug Instructions; "Sirmione (SERMION)", Dec. 2010, Russian Website at http://medi.ru/doc/g84neu68.htm; 11 pages.
Russian Office Action dated Apr. 1, 2015 for Application No. 2012147527, filed Nov. 8, 2012.
Japanese Office Action dated Apr. 6, 2015 for Application No. 2013-510322, filed May 12, 2011.
Bogardus et al., "Solubility of doxycycline in aqueous solutions" Journal of Pharmaceutical Sciences (1979) 68:188-194.

(Continued)

*Primary Examiner* — Jared D Barsky
(74) *Attorney, Agent, or Firm* — Knobbe, Martens, Olson & Bear LLP

(57) ABSTRACT

The present invention relates to compositions, pharmaceutical compositions, and methods for preparing the same, comprising a tetracycline with improved stability and solubility. Some embodiments include a tetracycline with an excess of a divalent or trivalent cation.

32 Claims, 7 Drawing Sheets

(56) References Cited

U.S. PATENT DOCUMENTS

| | | | |
|---|---|---|---|
| 2008/0020065 A1 | 1/2008 | Cherukuri | |
| 2008/0188445 A1 | 8/2008 | Muldoon et al. | |
| 2008/0233206 A1* | 9/2008 | Chomczynski | 424/641 |
| 2008/0248124 A1 | 10/2008 | Eguchi | |
| 2009/0035229 A1 | 2/2009 | Eirew | |
| 2009/0035393 A1 | 2/2009 | Geibel et al. | |
| 2009/0111780 A1 | 4/2009 | Giordano | |
| 2009/0275660 A1 | 11/2009 | Chauhan | |
| 2010/0010101 A1 | 1/2010 | Cherukuri | |
| 2010/0129448 A1 | 5/2010 | Talton | |
| 2011/0059177 A1 | 3/2011 | Thatte | |
| 2013/0040918 A1 | 2/2013 | Griffith et al. | |
| 2014/0194393 A1 | 7/2014 | Griffith et al. | |

FOREIGN PATENT DOCUMENTS

| | | | |
|---|---|---|---|
| CN | 1390550 | 1/2003 | |
| CN | 1562045 | 1/2005 | |
| CN | 101254156 | 9/2008 | |
| CN | 101607086 | 12/2009 | |
| CN | 101822650 | 9/2010 | |
| CN | 101940560 | 1/2011 | |
| DE | 1228252 | 1/1957 | |
| DE | 1053734 | 6/1957 | |
| DE | 1144721 | 4/1961 | |
| DE | 2659152 | 12/1976 | |
| EP | 0184389 | 6/1986 | |
| EP | 0271374 | 11/1987 | |
| EP | 0337733 | 10/1988 | |
| EP | 0536515 | 4/1993 | |
| EP | 1578434 | 9/2005 | |
| EP | 1902706 | 3/2008 | |
| ES | 324597 | 7/1989 | |
| GB | 793558 | 4/1958 | |
| GB | 809015 | 2/1959 | |
| GB | 812138 | 4/1959 | |
| GB | 845454 | 9/1960 | |
| GB | 879629 | 10/1961 | |
| GB | 901107 | 7/1962 | |
| GB | 901107 A * | 7/1962 | A61K 31/65 |
| GB | 947601 | 1/1964 | |
| GB | 948090 | 1/1964 | |
| GB | 1120821 | 7/1968 | |
| IN | 183807 | 4/2000 | |
| JP | 61130228 | 6/1986 | |
| JP | 11286448 | 10/1999 | |
| JP | 11292767 | 10/1999 | |
| JP | 2008-533146 | 8/2008 | |
| RU | 2163801 02 | 3/2001 | |
| RU | 2273232 C2 | 1/2005 | |
| RU | 2279292 C2 | 7/2006 | |
| WO | WO96/01634 | 1/1996 | |
| WO | WO 00/07601 | 2/2000 | |
| WO | WO 01/92288 | 12/2001 | |
| WO | WO 02/15848 | 2/2002 | |
| WO | WO 03/035030 | 5/2003 | |
| WO | WO 03/066064 | 9/2003 | |
| WO | WO 04/000223 | 12/2003 | |
| WO | WO 2004/004658 | 1/2004 | |
| WO | WO 2005/009416 | 2/2005 | |
| WO | WO 2005/011707 | 2/2005 | |
| WO | WO 2006/002868 | 1/2006 | |
| WO | WO 2006/078925 | 7/2006 | |
| WO | WO 2006/099258 | 9/2006 | |
| WO | WO 2006/130501 | 12/2006 | |
| WO | WO 2007/075794 | 7/2007 | |
| WO | WO 2008/121107 | 10/2008 | |
| WO | WO 2009/035818 | 3/2009 | |
| WO | WO 2009/059191 | 5/2009 | |
| WO | WO 2009/076454 | 6/2009 | |
| WO | WO 2009/120389 | 10/2009 | |
| WO | WO 2009/155931 | 12/2009 | |
| WO | WO 2010/022031 | 2/2010 | |
| WO | WO 2010/033800 | 3/2010 | |
| WO | WO 2010/034003 | 3/2010 | |
| WO | WO 2010/034011 | 3/2010 | |
| WO | WO 2010/046932 | 4/2010 | |
| WO | WO 2010/091124 | 8/2010 | |
| WO | WO 2011/008760 | 1/2011 | |

OTHER PUBLICATIONS

Chow et al., "Formulation of hydrophilic non-aqueous gel: drug stability in different solvents and rheological behavior of gel matrices", Pharm Res. (2008) 25(1):207-217. Epub Oct. 2, 2007.

Gonzales et al., "Effect of intravenous magnesium sulfate on chronic obstructive pulmonary disease exacerbations requiring hospitalization: a randomized placebo-controlled trial", Arch Bronconeumol. (2006) 42(10:491.

Jian-Chu et al., "A multi-center randomized clinical study of minocycline hydrochloride on the treatment of respiratory and urinary track infections", Chinese J Antibiot. (2008) 8:0483-0486, 0498.

Jochsberger T. "Differential Pulse Polarography of Tetracycline: Determination of Complexing Tendencies of Tetracycline Analogs in the Presence of Cations", Journal of Pharmaceutical Sciences 1 (1979) vol. 68 1061-1063.

Light et al., Laboratory and Animal Investigations: Comparison of the Effectiveness of Tetracycline and Minocycline as Pleural Sclerosing Agents in Rabbits*, Aug. 1994, pp. 577-582, 106 / 2; downloaded from http://journal.publications.chestnet.org, on May 9, 2013.

Mason et al., "Pharmacology of tetracycline water medication in swine", J Anim Sci (2009) 85:3179-3186.

Miyazaki et al., "A comparison of solubility characteristics of free bases and hydrochloride salts of tetracycline antibiotics in hycrochloric acid solutions" Chem. Pharm. Bull. (1975) 23:1197-1204.

Pawelczyk et al., "Kinetics of drug decomposition. Part 74. Kinetics of degradation of minocycline in aqueous solution", Pol J Pharmacol Pharm. (1982) 34(5-6):409-421.

Schramm, G., "Some Experiments on the Incompatibility of semisynthetic Tetracyclines", Schweizerische Apotheker-Zeitung (1976), 114(16), 361-6.

Triax Pharmaceuticals, LLC, Minocin® Minocycline for Injection 100 Mg/Vial Intravenous, Aug. 2010, pp. 3-19, Document No. NDA 50-444/S-047.

Xuan et al., "Hydrolysis and photolysis of oxytetracycline in aqueous solution", J Environ Scie Health, Part B (2010) 45(1):73-81.

Yamaguchi et al., "Transport of Divalent Cations with Tetracycline as Mediated by the Transposon Tn10-encoded Tetracycline Resistance Protein", J Biol Chem. (1990) 265(9):4809-4813.

International Search Report and Written Opinion dated Nov. 11, 2011 for International Patent Application No. PCT/US2011/036351, filed May 12, 2011.

International Preliminary Report on Patentability dated Jul. 31, 2012 for International Patent Application No. PCT/US2011/036351, filed May 12, 2011.

Chinese First Office Action dated Feb. 10, 2014 for Application No. 201180033194.X, filed Jan. 4, 2013.

Chinese First Office Action dated Nov. 3, 2014 for Application No. 201180033194.X, filed Jan. 4, 2013.

Columbian Technical Report/Search dated Jul. 11, 2014 for Application No. 12-225411, filed Dec. 12, 2012.

European Supplementary Search Report dated May 8, 2014 for Application No. 11781314.7, filed Dec. 10, 2012.

New Zealand Examination Report dated Jul. 11, 2013 for Application No. 603764, filed May 12, 2011.

New Zealand Further Examination Report dated Nov. 24, 2014 for Application No. 603764, filed May 12, 2011.

Singapore Search Report and Written Opinion dated Dec. 18, 2014 for Application No. 2012082905, filed May 12, 2011.

Stasiuk et al., "Modulation of Hemolytic Properties Cations", Cell Molec Biol Lttrs. (1996) 1:189-198.

(56) References Cited

OTHER PUBLICATIONS

Singapore 2nd Written Opinion dated Jun. 21, 2016 for Application No. 201208290-5, filed May 12, 2011.

* cited by examiner

TETRACYCLINE COMPOSITIONS

RELATED APPLICATIONS

This application is a continuation of U.S. application Ser. No. 13/654,018, filed Oct. 17, 2012, which is a continuation of International Application No. PCT/US2011/036351 filed on May 12, 2011, which claims priority to U.S. Provisional Application No. 61/392,304 filed Oct. 12, 2010, and to U.S. Provisional Application No. 61/334,106 filed May 12, 2010, the contents of which are incorporated herein by reference in their entireties.

FIELD OF THE INVENTION

The present invention relates to tetracycline compositions and methods for preparing and using the same. Some embodiments include a tetracycline with an excess of a divalent or trivalent cation.

BACKGROUND OF THE INVENTION

Tetracyclines are used as broad spectrum antibiotics to treat various bacterial infections, such as infections of the respiratory tract, sinuses, middle ear, urinary tract, and intestines, and can be used in the treatment of gonorrhoea, especially in patients allergic to β-lactams and macrolides. Tetracyclines interfere with the protein synthesis of Gram positive and Gram-negative bacteria by preventing the binding of aminoacyl-tRNA to the ribosome. The action of tetracyclines is bacteriostatic (preventing growth of bacteria) rather than killing (bactericidal).

Tetracyclines degrade rapidly to form epitetracycline, anhydrotetracycline, epianhydrotetracycline, and other degradation products. Once degraded, tetracyclines have small therapeutic value, since the degradation products have no therapeutically useful activity. Degradation begins as soon as the antiobiotic is in solution, and continues until reaching an equilibrium of antibiotic and epimer concentrations. The equilibrium point is temperature and pH dependent, with more epimer being formed at higher temperatures and lower pH. Oxidation and other side reactions cause further degradation. Thus, tetracyclines can have a limited existence in aqueous environments in their active form. Moreover, the degradation products of tetracyclines are toxic and can cause Fanconi syndrome, a potentially fatal disease affecting proximal tubular function in the nephrons of the kidneys.

There is a need to provide hospital staff with the flexibility and advantages that come with longer admixture and reconstitution times without the need for refrigeration so that for instance, a hospital pharmacist could prepare a solution the day before it is needed. Furthermore, often after a natural disaster such as hurricanes, earthquakes, or tsunamis, access to refrigeration equipment can be scarce and may be further impeded by the lack of electricity. Stable formulations of tetracyclines could be stored as a solution, negating the need for reconstitution, and allowing its use in inhalers or nebulizers for outpatient use.

In addition, some tetracyclines can cause tetracycline-induced hemolysis. This hemolysis can lead to venous phlebitis at the site of injection when administered intravenously, resulting in irritation and potentially limiting the volumes of infusion that can be tolerated. Thus, there is a need for formulations of such tetracyclines that reduce the incidence of hemolysis.

SUMMARY OF THE INVENTION

The present invention relates to tetracycline compositions and methods for preparing and using the same. Some embodiments include a tetracycline with an excess of a divalent or trivalent cation.

Some embodiments include pharmaceutical compositions. In some embodiments the pharmaceutical compositions comprise an aqueous solution of minocycline and a divalent or trivalent cation, wherein the molar ratio of divalent or trivalent cation to minocycline is greater than 2:1 and wherein the solution does not comprise a pharmaceutically acceptable oil and is suitable for intravenous administration.

In some embodiments the pharmaceutical compositions comprise an aqueous solution of minocycline and a divalent or trivalent cation, wherein the molar ratio of divalent or trivalent cation to minocycline is greater than 2:1 and wherein the solution has a pH greater than 4 and less than 5 and is suitable for intravenous administration.

In some embodiments the pharmaceutical compositions comprise an aqueous solution of a 7-dimethylamino-tetracycline antibiotic and a divalent or trivalent cation, wherein the molar ratio of divalent or trivalent cation to 7-dimethylamino-tetracycline antibiotic is greater than 3:1 and wherein the solution does not comprise a pharmaceutically acceptable oil, gluconate, or a pyridine-containing compound, has a pH greater than 2 and less than 7, and is suitable for intravenous administration.

In some embodiments, the solution does not comprise polyoxyethylene hydrogenated castor oil.

In some embodiments, the solution does not comprise an antioxidant.

In some embodiments, the solution does not comprise a pyridine-containing compound.

In some embodiments, the solution does not comprise nicotinamide.

In some embodiments, the solution does not comprise an alcohol.

In some embodiments, the solution does not comprise glycerol.

In some embodiments, the solution does not comprise polyethylene glycol.

In some embodiments, the solution does not comprise gluconate.

In some embodiments, the solution does not comprise a pyrrolidone compound.

In some embodiments, the solution does not comprise a water-miscible local anaesthetic.

In some embodiments, the water-miscible local anaesthetic is procaine.

In some embodiments, the solution does not comprise urea.

In some embodiments, the solution does not comprise lactose.

In some embodiments, the solution does not comprise a dehydrating agent. In some embodiments, the dehydrating agent is selected from the group consisting of ethyl acetate, acetic anhydride, absolute ethanol, ethyl acetate, acetic anhydride, and mixtures thereof.

In some embodiments, the solution has a pH of less than 7. In some embodiments, the solution has a pH of less than 6. In some embodiments, the solution has a pH of less than 5.

In some embodiments, the solution has a pH greater than 2 and less than 7. In some embodiments, the solution has a pH greater than 4 and less than 7. In some embodiments, the solution has a pH greater than 4 and less than 6. In some embodiments, the solution has a pH greater than 4 and less than 5.

In some embodiments, the molar ratio of divalent or trivalent cation to minocycline is greater than 3:1. In some embodiments, the molar ratio of divalent or trivalent cation to minocycline is greater than 5:1. In some embodiments, the molar ratio of divalent or trivalent cation to minocycline is greater than 8:1. In some embodiments, the molar ratio of divalent or trivalent cation to minocycline is greater than 10:1.

In some embodiments, the osmolality of the solution is less than 500 mOsm/kg. In some embodiments, the osmolality of the solution is less than 400 mOsm/kg. In some embodiments, the osmolality of the solution is less than 350 mOsm/kg.

In some embodiments, the concentration of minocycline is at least 1 mg/ml. In some embodiments, the concentration of minocycline is at least 5 mg/ml. In some embodiments, the concentration of minocycline is at least 10 mg/ml.

In some embodiments, the solution comprises magnesium sulfate. In some embodiments, the solution comprises magnesium oxide. In some embodiments, the solution comprises magnesium acetate. In some embodiments, the solution comprises magnesium chloride.

In some embodiments, the solution comprises a buffer. In some embodiments, the solution comprises acetate.

In some embodiments, the solution comprises a base. In some embodiments, the base comprises NaOH.

In some embodiments, the cation is selected from iron, copper, zinc, manganese, nickel, cobalt, aluminum, calcium, magnesium and gallium. In some embodiments, the cation is selected from magnesium, calcium, and zinc. In some embodiments, the cation is magnesium.

In some embodiments, the 7-dimethylamino-tetracycline is selected from minocycline, PTK796, and a glycylcycline. In some embodiments, the glycylcycline is tigecycline. In some embodiments, the 7-dimethylamino-tetracycline is minocycline. In some embodiments, the 7-dimethylamino-tetracycline is PTK796.

Some embodiments include pharmaceutical compositions comprising 10 mg/ml minocycline, $MgCl_2$, and NaOH, wherein the Mg to minocycline molar ratio is 5:1, and the pH is greater than 4.5 and less than 5.5.

Some embodiments include pharmaceutical compositions comprising 10 mg/ml minocycline, $MgSO_4$, and sodium acetate, wherein the Mg to minocycline molar ratio is 5:1, the pH is greater than 4.5 and less than 5.5, and the osmolality is greater than 275 mOsm/kg and less than 375 mOsm/kg.

Some embodiments include pharmaceutical compositions comprising 10 mg/ml minocycline and $Mg(C_2H_3O_2)_2$, wherein the Mg to minocycline molar ratio is 5:1, and the pH is greater than 4.5 and less than 5.5.

Some embodiments include pharmaceutical compositions comprising 10 mg/ml minocycline, $MgSO_4$, and NaOH, wherein the Mg to minocycline molar ratio is 5:1, the pH is greater than 4.5 and less than 5.5, and the osmolality is greater than 150 mOsm/kg and less than 250 mOsm/kg.

Some embodiments include pharmaceutical compositions comprising 5 mg/ml tigecycline, $MgSO_4$, and NaOH, wherein the Mg to tigecycline molar ratio is 5:1, and the pH is greater than 5.5 and less than 6.5.

Some embodiments include pharmaceutical compositions comprising 5 mg/ml tigecycline, $MgSO_4$, and NaOH, wherein the Mg to tigecycline molar ratio is 12:1, and the pH is greater than 5.5 and less than 6.5.

Some embodiments include pharmaceutical compositions comprising 5 mg/ml tigecycline, $MgCl_2$, and NaOH, wherein the Mg to tigecycline molar ratio is 5:1, and the pH is greater than 5.5 and less than 6.5.

Some embodiments include pharmaceutical compositions comprising 5 mg/ml tigecycline, $MgCl_2$, and NaOH, wherein the Mg to tigecycline molar ratio is 12:1, and the pH is greater than 5.5 and less than 6.5.

Some embodiments include pharmaceutical compositions suitable for topical administration comprising 5 mg/ml tigecycline, $MgSO_4$, and NaOH, wherein the Mg to tigecycline molar ratio is 5:1, and the pH is greater than 6.0 and less than 7.0.

Some embodiments include pharmaceutical compositions suitable for topical administration comprising 5 mg/ml tigecycline, $MgSO_4$, and NaOH, wherein the Mg to tigecycline molar ratio is 12:1, and the pH is greater than 6.0 and less than 7.0.

Some embodiments include pharmaceutical compositions suitable for topical administration comprising 5 mg/ml tigecycline, $CaCl_2$, and NaOH, wherein the Ca to tigecycline molar ratio is 5:1, and the pH is greater than 6.0 and less than 7.0.

Some embodiments include pharmaceutical compositions suitable for topical administration comprising 5 mg/ml tigecycline, $CaCl_2$, and NaOH, wherein the Ca to tigecycline molar ratio is 12:1, and the pH is greater than 6.0 and less than 7.0.

Some embodiments include water-soluble solid compositions comprising minocycline or a salt thereof and a salt that comprises a divalent or trivalent cation.

Some embodiments include water-soluble solid compositions comprising a 7-dimethylamino-tetracycline antibiotic or a salt thereof and a salt comprising a divalent or trivalent cation, wherein the molar ratio of divalent or trivalent cation to 7-dimethylamino-tetracycline antibiotic is greater than 3:1 and wherein the composition does not comprise gluconate or a pyridine-containing compound.

In some embodiments, the molar ratio of divalent or trivalent cation to minocycline is greater than 1:1. In some embodiments, the molar ratio of divalent or trivalent cation to minocycline is greater than 2:1. In some embodiments, the molar ratio of divalent or trivalent cation to minocycline is greater than 3:1. In some embodiments, the molar ratio of divalent or trivalent cation to the minocycline or the 7-dimethylamino-tetracycline antibiotic is greater than 5:1. In some embodiments, the molar ratio of divalent or trivalent cation to the minocycline or the 7-dimethylamino-tetracycline antibiotic is at greater than 8:1. In some embodiments, the molar ratio of divalent or trivalent cation to the minocycline or the 7-dimethylamino-tetracycline antibiotic is greater than 10:1.

Some embodiments include compositions in the form of a lyophile.

In some embodiments, the salt is magnesium sulfate.

In some embodiments, the salt is calcium chloride.

In some embodiments, the composition comprises sodium acetate.

In some embodiments, the composition comprises NaOH.

In some embodiments, the salt is selected from magnesium chloride, magnesium bromide, magnesium sulfate, calcium chloride, calcium bromide, calcium sulfate, zinc chloride, gallium chloride, magnesium malate, magnesium citrate, magnesium acetate, calcium citrate, zinc acetate, and zinc citrate.

In some embodiments, the composition does not comprise an antioxidant.

In some embodiments, the composition does not comprise a pyridine-containing compound. In some embodiments, the composition does not comprise nicotinamide.

In some embodiments, the composition does not comprise gluconate.

In some embodiments, the 7-dimethylamino-tetracycline is selected from minocycline, PTK796, and a glycylcycline. In some embodiments, the glycylcycline is tigecycline. In some embodiments, the 7-dimethylamino-tetracycline is minocycline. In some embodiments, the 7-dimethylamino-tetracycline is PTK796.

Some embodiments include methods for preparing a pharmaceutical composition comprising dissolving the water-soluble solid composition of any one of the water-soluble solid compositions provided herein in water to form a solution Some embodiments include methods for preparing a pharmaceutical composition comprising dissolving a 7-dimethylamino-tetracycline in a solution comprising a divalent or trivalent cation.

Some embodiments include methods for preparing a pharmaceutical composition comprising dissolving a 7-dimethylamino-tetracycline in a solution comprising a divalent or trivalent cation; adjusting the pH of the solution; and lyophilizing the composition.

In some embodiments, the 7-dimethylamino-tetracycline is selected from minocycline, PTK796, and a glycylcycline. In some embodiments, the glycylcycline is tigecycline.

In some embodiments, the pH of the solution is adjusted to be less than 6. In some embodiments, the pH of the solution is adjusted to be less than 5.

In some embodiments, the pH of the solution is adjusted to be greater than 2 and less than 7. In some embodiments, the pH of the solution is adjusted to be greater than 4 and less than 7. In some embodiments, the pH of the solution is adjusted to be greater than 4 and less than 6. In some embodiments, the pH of the solution is adjusted to be greater than 4 and less than 5.

In some embodiments, adjusting the pH comprises adding an acid. In some embodiments, the acid is HCl.

In some embodiments, adjusting the pH comprises adding a base. In some embodiments, the base is NaOH.

In some embodiments, adjusting the pH comprises forming a buffer. In some embodiments, forming the buffer comprises adding sodium acetate.

In some embodiments, the divalent or trivalent cation is selected from iron, copper, zinc, manganese, nickel, cobalt, aluminum, calcium, magnesium and gallium. In some embodiments, the cation is selected from magnesium, calcium, and zinc. In some embodiments, the cation is magnesium.

Some embodiments include kits comprising a first container comprising a diluent that comprises an aqueous solution of a divalent or trivalent cation; and a second container comprising a solid composition soluble in the diluent, wherein the solid composition comprises minocycline in an amount such that the molar ratio of the divalent or trivalent cation to minocycline is greater than 2:1.

Some embodiments include kits comprising a first container comprising a diluent that comprises an aqueous solution of a divalent or trivalent cation; and a second container comprising a solid composition soluble in the diluent, wherein the solid composition comprises a 7-dimethylamino-tetracycline antibiotic in an amount such that the molar ratio of the divalent or trivalent cation to 7-dimethylamino-tetracycline antibiotic is greater than 3:1.

In some embodiments, the diluent comprises an acid. In some embodiments, the acid is HCl.

In some embodiments, the diluent comprises a base. In some embodiments, the base is NaOH.

In some embodiments, the diluent comprises a buffer. In some embodiments, the diluent comprises sodium acetate.

In some embodiments, the pH of the diluent is greater than pH 6 and less than pH 8.

In some embodiments, the divalent or trivalent cation is selected from iron, copper, zinc, manganese, nickel, cobalt, aluminum, calcium, magnesium and gallium. In some embodiments, the cation is selected from magnesium, calcium, and zinc. In some embodiments, the cation is magnesium.

In some embodiments, the molar ratio of divalent or trivalent cation to minocycline is greater than 3:1. In some embodiments, the molar ratio of divalent or trivalent cation to the minocycline or the 7-dimethylamino-tetracycline antibiotic is greater than 5:1. In some embodiments, the molar ratio of divalent or trivalent cation to the minocycline or the 7-dimethylamino-tetracycline antibiotic is at greater than 8:1. In some embodiments, the molar ratio of divalent or trivalent cation to the minocycline or the 7-dimethylamino-tetracycline antibiotic is greater than 10:1.

In some embodiments, the 7-dimethylamino-tetracycline is selected from minocycline, PTK796, and a glycylcycline. In some embodiments, the glycylcycline is tigecycline. In some embodiments, the 7-dimethylamino-tetracycline is minocycline. In some embodiments, the 7-dimethylamino-tetracycline is PTK796.

Some embodiments include methods of treating or preventing a bacterial infection in a subject, comprising administering the pharmaceutical composition of any one of the pharmaceutical compositions provided herein to the subject via an intravenous route.

Some embodiments include methods of treating or preventing a bacterial infection in a subject, comprising administering the pharmaceutical composition made according to any one of the methods of preparing a pharmaceutical compositions provided herein to the subject via an intravenous route.

In some embodiments, the intravenous administration includes administering less than 200 ml of the composition.

In some embodiments, the intravenous administration includes administering the composition in less than 60 minutes.

Some embodiments include methods of treating or preventing a bacterial infection in a subject, comprising administering the pharmaceutical composition of any one of the pharmaceutical compositions provided herein to the subject via a topical route.

Some embodiments include methods of treating or preventing a bacterial infection in a subject, comprising administering the pharmaceutical composition made according to any one of the methods of preparing a pharmaceutical compositions provided herein to the subject via a topical route.

Some embodiments include compositions comprising tigecycline and a divalent or trivalent cation, wherein the molar ratio of said divalent or trivalent cation to said tigecycline is greater than 1:1.

In some embodiments, the tigecycline and divalent or trivalent cation are in aqueous solution.

In some embodiments, the molar ratio of said divalent or trivalent cation to said tigecycline is greater than 3:1.

DETAILED DESCRIPTION

Figure 1:
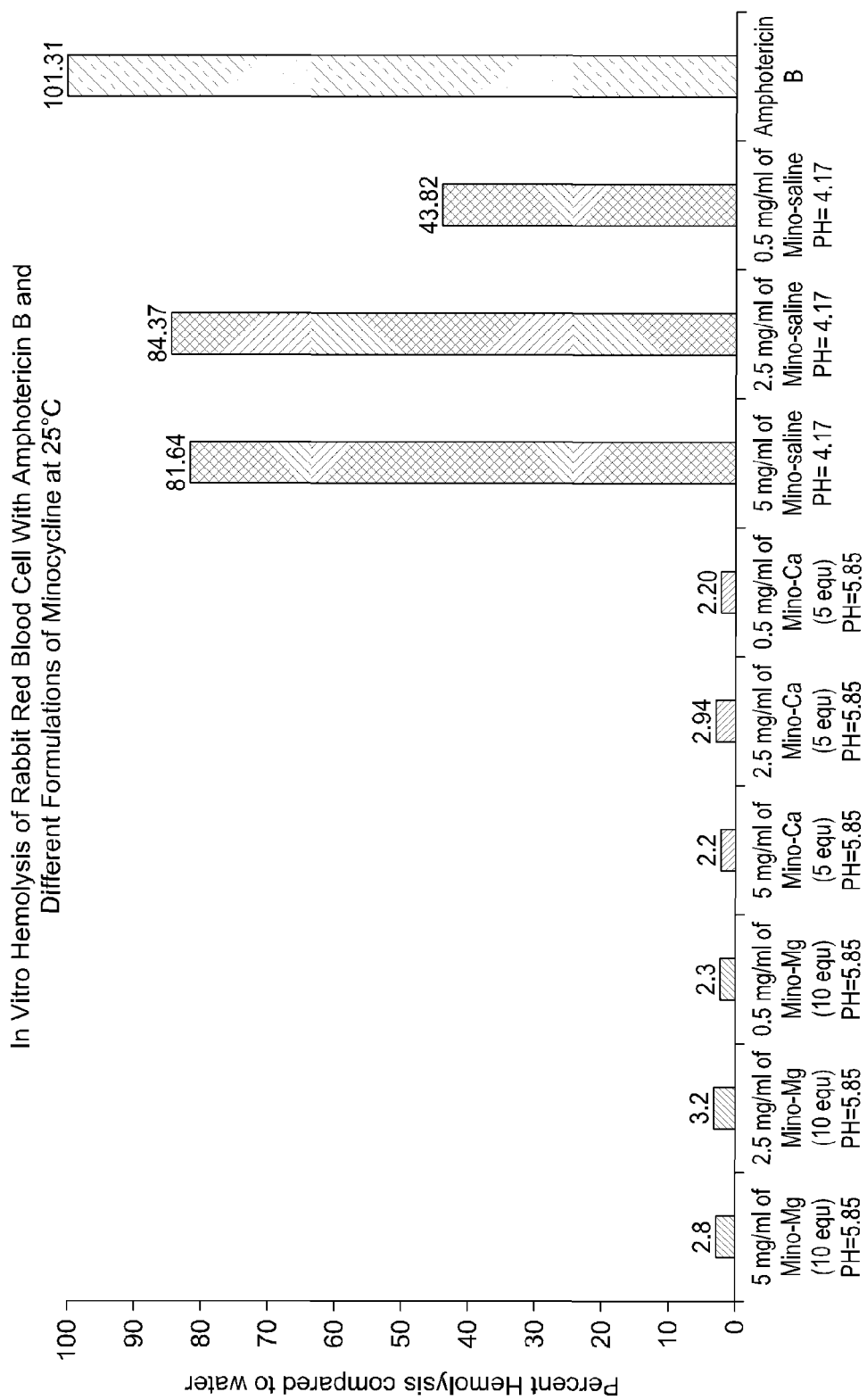
FIG. 1 shows a graph of percent hemolysis of rabbit red blood cells incubated with various concentrations of minocycline in various solutions relative to hemolysis in water, in which the minocycline solutions formulated with divalent cations were adjusted to ph 5.85.

The present invention relates to tetracycline compositions and methods for preparing and using the same. Some embodiments include a tetracycline with an excess of a metal cation. In some embodiments, the compositions have improved stability against both oxidative degradation and epimerization. Some such compositions are therefore more stable when dissolved, lyophilized, reconstituted, and/or diluted than other compositions. Some embodiments also provide compositions having a lower level of tetracycline-induced hemolysis and resulting phlebitis.

It was unexpectedly discovered that the incidence of tetracycline-induced hemolysis can be greatly decreased by formulating the tetracycline with divalent or trivalent cations. In some embodiments, high molar ratios of divalent or trivalent cations to tetracycline antibiotics significantly decreases hemolysis.

It was also unexpectedly discovered that the stability of aqueous solutions of tetracyclines can be greatly increased by the addition of divalent or trivalent cations. In some embodiments, the stability of aqueous solutions of tetracyclines increase with higher molar ratios of divalent or trivalent cations to tetracycline. Indeed, some such solutions were found to be stable for several weeks at 37° C.

In certain compositions, the solubility of a tetracycline antibiotic is decreased in an aqueous solution comprising a multivalent cation. It has been unexpectedly discovered that increasing the molar ratio of multivalent cation to such tetracycline antibiotics can increase the solubility of the tetracycline. Accordingly, some embodiments described herein provide solutions of a tetracycline with improved solubility.

Compositions

Some embodiments include compositions comprising a tetracycline antibiotic or a salt thereof in combination with a divalent or trivalent cation. Tetracyclines include a family of structurally-related compounds that may have broad-spectrum antibiotic activities. Examples of tetracyclines include Tetracycline, Chlortetracycline, Oxytetracycline, Demeclocycline, Doxycycline, Lymecycline, Meclocycline, Methacycline, Minocycline, Rolitetracycline, Minocycline, Tigecycline, Chlorocycline, Glycylcyclines, Aminomethylcyclines, TP434, and PTK796, (also known as BAY 73-7388 and MK2764). The structure of TP434 is provided below:

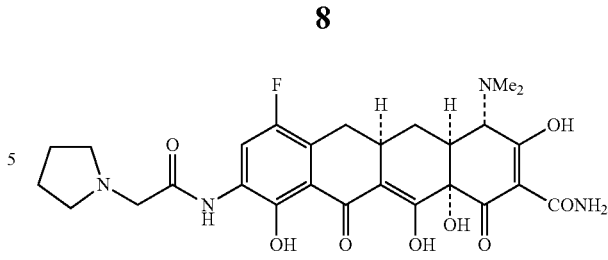

In one embodiment, the tetracycline antibiotic is selected from the group consisting of tetracycline, oxytetracycline, doxycycline, chlorocycline, minocycline, glycylcyclines and aminomethylcyclines. In one embodiment, the tetracycline is a glycylcycline. In one embodiment, the glycylcycline is tigecycline. In one embodiment, the tetracycline is an aminomethylcycline. In one embodiment, the aminomethylcycline is PTK796, also known as BAY 73-7388 and MK2764. In another embodiment, the tetracycline is selected from the group consisting of tetracycline, minocycline, tigecycline and PTK796. In one embodiment, the tetracycline antibiotic is tetracycline. In one embodiment, of the invention, the tetracycline is minocycline. In one embodiment, of the invention, the tetracycline is tigecycline. In yet another embodiment, of the invention, the tetracycline is PTK796. Some embodiments include a salt of a tetracycline antibiotic.

In some embodiments, the tetracycline antibiotic is a 7-dimethylamino-tetracycline. 7-dimethylamino-tetracyclines contain an additional dimethylamino substituent at the 7-position on the four-ring core. The 7-position is indicated on following numbered structure of minocycline:

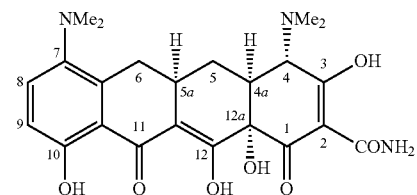 [SMILES: CN(C)c1ccc(O)c2c1C[C@H]1C[C@H]3[C@H](N(C)C)C(O)=C(C(N)=O)C(=O)[C@@]3(O)C(O)=C1C2=O]

Examples of 7-dimethylamino-tetracyclines include minocycline, a glycylcycline (e.g., tigecycline) and PTK796. Example structures of such compounds include:

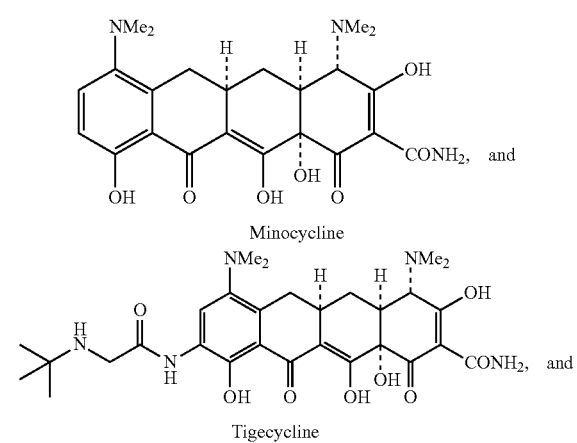

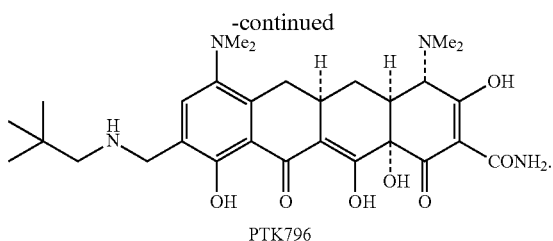

PTK796

As used herein, "glycylcyclines" are 7-dimethylamino-tetracyclines having an N-alkylglycylamido side chain at position 9 of the four-ring core.

In some embodiments, the 7-dimethylamino-tetracycline antibiotic has the structure:

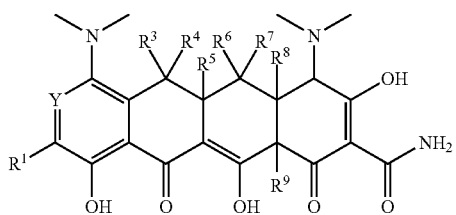

or tautomers thereof, wherein:
$R^1$ is selected from H, —$(CH_2)_n$NHC(O)$(CH_2)_n R^{10}$, and —$(CH_2)_n R^{10}$, where each n is independently an integer from 0 to 3, and
$R^{10}$ is selected from —NH—$C_{1-8}$alkyl, —NH—$C_{1-8}$cycloalkyl, and a saturated 4-to-7-membered heterocycle containing one nitrogen atom, wherein if the connecting atom of $R^{10}$ is carbon, the nitrogen atom is optionally substituted by $C_1$-$C_4$alkyl;
Y is $CR^2$ or N; and
$R^2$, $R^3$, $R^4$, $R^5$, $R^6$, $R^7$, $R^8$, and $R^9$ are each independently selected from H, —OH, halogen, and $C_{1-4}$ alkyl; or
optionally $R^1$ and $R^2$ together form a 6-membered aryl or heteroaryl ring, optionally substituted by one or two groups independently selected from H, $R^1$, —OH, halogen, and $C_{1-4}$ alkyl.

In some embodiments, each of $R^3$, $R^4$, $R^5$, $R^6$, $R^7$, $R^8$, and $R^9$ are hydrogen.

As used herein, "alkyl" refers to a straight- or branched-chain moiety containing only carbon and hydrogen. Alkyls may have any degree of saturation. Examples include methyl, ethyl, propyl, isopropyl, butyl, isobutyl, and tertbutyl.

As used herein, "cycloalkyl" refers to a ring or ring system comprising only carbon in the ring backbone. Cycloalkyls may include one or more fused or bridged rings. Cycloalkyls may have any degree of saturation provided that at least one ring is not aromatic. Examples include cyclopropyl, cyclobutyl, cyclopentyl, cyclohexyl, and cyclohexenyl.

As used herein, "heterocycle" refers to a ring or ring system comprising at least one heteroatom in the ring backbone. Heterocycles may include one or more fused or bridged rings. Heterocycles may have any degree of saturation provided that at least one ring is not aromatic. Examples include pyrrolidine, piperidine, piperazine, and morpholino.

As used herein, "aryl" refers to an aromatic ring or ring system comprising only carbon in the ring backbone. Aryls may include one or more fused rings. Examples include phenyl and naphthyl.

As used herein, "heteroaryl" refers to an aromatic ring or ring system comprising at least one heteroatom in the ring backbone. Heteroaryls may include one or more fused rings. Examples include imidazole, oxazole, pyridine, and quinoline.

Some compositions include at least one multivalent cation. Multivalent cations include bivalent and trivalent cations, e.g., metal cations. The metal cations include common multivalent metal cations. In some embodiments, the metal cations include iron, copper, zinc, manganese, nickel, cobalt, aluminum, calcium, magnesium and gallium.

Some compositions include a salt that comprises the cation. In one embodiment, the salts are inorganic metal salts and can include anhydrous, hydrated and solvated forms of the salts. In another embodiment, the salts are organic metal salts and include but are not limited to the anhydrous, hydrated and solvated forms of the salt. In one embodiment, the anion in the inorganic metal salts can include chloride, bromide, oxide, and sulfate salts. In one embodiment, the organic metal salts are those where the anion of the salt is selected from the GRAS (generally regarded as safe) list such as but not limited to acetate, citrate, gluconate, and malate salts. Suitable anions may also be found in see Remington's Pharmaceutical Sciences, Mack Publishing Company, Easton, Pa. In some embodiments, a composition can include more than one type of metal cation. In some such embodiments, the anions for each metal salt can be the same. In another embodiment, the anions for each metal salt are different. In another embodiment, the metal cation is included in the compositions provided herein as different salts of the same cation. In one embodiment the metal salts are all inorganic. In another embodiment, the metal salts are all organic. In yet another embodiment, the metal salts are a combination of organic and inorganic salts.

Examples of inorganic metal salts that may be included in the compositions provided herein include magnesium chloride (including the hexahydrate), magnesium bromide, magnesium sulfate (including the heptahydrate), magnesium oxide, calcium chloride, calcium bromide, calcium sulfate, zinc chloride, and gallium chloride. Examples of inorganic metal salts that may be included in the compositions provided herein include magnesium malate, magnesium gluconate, magnesium citrate, magnesium acetate (including the trihydrate), calcium gluconate, calcium citrate, zinc gluconate, zinc acetate, and zinc citrate. The salts described herein include both their anhydrous and hydrated forms.

Some compositions provided herein include a tetracycline and divalent or trivalent cation, e.g., metal cation at particular molar ratios of divalent or trivalent cation to tetracycline. For example, some embodiments include compositions comprising a tetracycline and a divalent or trivalent cation, wherein the molar ratio of said divalent or trivalent cation to said tetracycline is greater than about 1:1. In some such embodiments, the molar ratio of the divalent or trivalent cation to the tetracycline is greater than about 2:1, greater than about 3:1, greater than about 4:1, greater than about 5:1, greater than about 6:1, greater than about 7:1, greater than about 8:1, greater than about 9:1, greater than about 10:1, greater than about 11:1, greater than about 12:1, greater than about 13:1, greater than about 14:1, greater than about 15:1, greater than about 16:1, greater than about 17:1, greater than about 18:1, greater than about 19:1, greater than about 20:1, greater than about 21:1, greater than about 22:1, greater than about 23:1, greater than about 24:1, greater than about 25:1, greater than about 26:1, greater than about 27:1, greater than about 28:1, greater than about 29:1, and greater than about 30:1. In some embodiments, the molar ratio is greater than about 35:1, greater than about 40:1, greater than about 45:1, and greater than about 50:1, In some such embodiments, the molar ratio of the divalent or trivalent cation to the tetracycline is between about 1:1 to about 30:1, between about 5:1 to about 30:1, between about 10:1 to about 30:1, and between about 20:1 to about 30:1. In some such embodiments, the molar ratio of the divalent or trivalent cation to the tetracycline is between about 1:1 to about 50:1, between about 5:1 to about 50:1, between about 10:1 to about 50:1, and between about 20:1 to about 50:1.

In some embodiments, the relative amounts of metal cation present in the compositions of the invention are those amounts which are in excess of the 1:1 metal cation: a tetracycline stoichiometry for each metal cation. In one embodiment of the invention, the metal cation to a tetracycline molar ratio ranges from 5:1 to 100:1. In another embodiment of the invention, the metal cation to a tetracycline molar ratio ranges from 5:1 to 50:1. In yet another embodiment of the invention, the metal cation to a tetracycline molar ratio ranges from 5:1 to 30:1. In one embodiment of the invention, the metal cation to a tetracycline molar ratio ranges from 5:1 to 10:1. In one embodiment of the invention, the metal cation to a tetracycline molar ratio ranges from 10:1 to 20:1. In one embodiment of the invention, the metal cation to a tetracycline molar ratio ranges from 10:1 to 15:1. In one embodiment of the invention, the metal cation to a tetracycline molar ratio is 5:1. In one embodiment of the invention, the metal cation to a tetracycline molar ratio is 10:1. In one embodiment of the invention, the metal cation to a tetracycline molar ratio is 12:1. In one embodiment of the invention, the metal cation to a tetracycline molar ratio is 15:1. In one embodiment of the invention, the metal cation to a tetracycline molar ratio is 20:1. In one embodiment of the invention, the metal cation to a tetracycline molar ratio is 30:1.

Some compositions include carbohydrates in addition to a divalent or trivalent cation. Suitable carbohydrates are those carbohydrates capable of reducing degradation of the tetracycline in at least one solid form prepared in at least one pH environment when compared to a solid form of a tetracycline prepared at the same pH environment lacking suitable carbohydrates. In one embodiment, the pH environment ranges from 3.0 to about 7.0, such as pHs ranging from about 4.0 to about 6.5, from about 5.0 to about 6.5, and from about 5.5 to about 6.5. In one embodiment, at least one solid form is chosen from powders and lyophilized cakes of a tetracycline. In another embodiment of the invention, carbohydrates are those carbohydrates capable of reducing degradation of the tetracycline in solution prepared in at least one pH environment when compared to a solution of a tetracycline prepared at the same pH environment lacking suitable carbohydrates. In one embodiment, the pH environment ranges from 3.0 to about 7.0, such as pHs ranging from about 4.0 to about 6.5, from about 5.0 to about 6.5, and from about 5.5 to about 6.5.

Suitable carbohydrates include mono and disaccharides e.g. an aldose monosaccharide or a disaccharide. Examples of suitable carbohydrates include but are not limited to the anhydrous, hydrated and solvated forms of compounds such as trehalose, lactose, mannose, sucrose and glucose. In one embodiment of the invention, the carbohydrate is a disaccharide. In another embodiment of the invention, the disaccharide is trehalose, lactose or sucrose. In yet another embodiment of the invention, the carbohydrate is lactose, including its different forms such as anhydrous lactose, lactose monohydrate or any other hydrated or solvated form of lactose. In one embodiment of the invention, the carbohydrate is trehalose, including its different forms such as anhydrous trehalose, trehalose dihydrate or any other hydrated or solvated form of trehalose.

In one embodiment of the invention, the suitable carbohydrate used is lactose monohydrate and the molar ratio of tigecycline to lactose monohydrate in the lyophilized powder or cake is between 1:0.2 to about 1:5. In another embodiment of the invention, the tigecycline to lactose monohydrate molar ratio is between 1:1.6 to about 1:3.3.

Some compositions include an antioxidant. Antioxidants can be used to prevent or reduce the oxidation of tetracyclines either in solution or in the solid state. Examples of antioxidants include ascorbic acid, citric acid, trehalose, butylated hydroxyl toluene (BHT), butylated hydroxyl anisole (BHA), sodium metabisulfite, d,l-α-tocopherol, and gentisic acid.

It will be appreciated that the compositions provided herein can include aerosols, liquids, and solids. Solids can include, for example, lyophilized compositions, such as powders, cakes, or the like. Such solids may be water soluble so that they may be used to prepare aqueous solutions. Liquids can include solutions or suspensions, which may be prepared from solid compositions. Liquids include solutions that may be prepared prior to manufacturing procedures such as lyophilization. In one embodiment, the solution may be stored for several hours prior to lyophilization in order to provide greater manufacturing flexibility. Liquids also include solutions that are prepared by reconstitution for use in administration to a patient. Some compositions include solutions made from the lyophilized powder or cake by, for example, reconstitution with saline or other pharmaceutically acceptable diluents. Pharmaceutically acceptable diluents are those listed by USP such as but not limited to water for injection, saline solution, lactated Ringer's solution for injection or dextrose solution. Some compositions include solutions resulting from diluting those reconstituted solutions with pharmaceutically acceptable diluents for use in intravenous bags.

In some embodiments, the pH of a liquid composition provided herein, such as an aqueous solution, is between about pH 2.0 to about pH 8.0, between about pH 2.5 to about pH 7.5. In some embodiments, the pH of the composition is between about pH 3.0 to about pH 7.0, between about pH 3.5 to about pH 6.5, between about pH 4.0 to about pH 6.5, between about pH 4.0 to about pH 6.0, between about pH 4.5 to about pH 6.0, between about pH 4.5 to about pH 5.5, between about pH 5.0 to about pH 5.5, between about pH 5.5 to about pH 6.5, between about pH 3.5 to about pH 4.5. In some embodiments, the pH of the solution is less than pH 7, less than pH 6, less than pH 5, less than pH 4, less than pH 3, and less than pH 2. In some embodiments the pH of the solution is greater than pH 2 and less than pH 7, greater than pH 4 and less than pH 7, greater than pH 4 and less than pH 6, and greater than pH 4 and less than pH 5.

In some embodiments, liquid compositions, such as an aqueous solution, can have an osmolality from about 300 mOsmol/kg to about 500 mOsmol/kg, from about 325 mOsmol/kg to about 450 mOsmol/kg, from about 350 mOsmol/kg to about 425 mOsmol/kg, or from about 350 mOsmol/kg to about 400 mOsmol/kg. In some embodiments, the osmolality of the formulation is greater than about 300 mOsmol/kg, about 325 mOsmol/kg, about 350 mOsmol/kg, about 375 mOsmol/kg, about 400 mOsmol/kg, about 425 mOsmol/kg, about 450 mOsmol/kg, about 475 mOsmol/kg, or about 500 mOsmol/kg. In some embodiments, liquid compositions can have an osmolality from about 200 mOsmol/kg to about 1250 mOsmol/kg. In another embodiment, the osmolality is between about 250 mOsmol/kg and about 1050 mOsmol/kg. In another embodiment, the osmolality is between about 250 mOsmol/kg and about 750 mOsmol/kg. In another embodiment, the osmolality is between about 350 mOsmol/kg and about 500 mOsmol/kg. In some embodiments, the osmolality of the solution is less than 500 mOsmol/kg, 450 mOsmol/kg, 400 mOsmol/kg, 350 mOsmol/kg, or 300 mOsmol/kg.

Some embodiments include an aqueous solution comprising a tetracycline having a concentration of at least 1 mg/ml, 5 mg/ml, 10 mg/ml, 15 mg/ml, 20 mg/ml, 25 mg/ml, 30 mg/ml, 35 mg/ml, 40 mg/ml, 45 mg/ml, or 50 mg/ml.

Some embodiments include an aqueous solution comprising a buffer, such as an acetate buffer (e.g., provided as sodium acetate), wherein the acetate has a concentration of at least 0.01 M, 0.02 M, 0.03 M, 0.04 M, 0.05 M, 0.1 M, 0.15 M, 0.20 M, 0.25 M, 0.30 M, 0.35 M, 0.40 M, 0.45 M, 0.50 M, 0.55 M, 0.60 M, 0.65 M, 0.70 M, 0.75 M, 0.80 M, 0.85 M, 0.90 M, or 0.95 M.

Some embodiments include an aqueous solution comprising a salt comprising divalent or trivalent cation, such as a magnesium salt (e.g., magnesium chloride or magnesium sulfate), having a concentration of at least 0.01 M, 0.02 M, 0.03 M, 0.04 M, 0.05 M, 0.1 M, 0.15 M, 0.20 M, 0.25 M, 0.30 M, 0.35 M, 0.40 M, 0.45 M, 0.50 M, 0.55 M, 0.60 M, 0.65 M, 0.70 M, 0.75 M, 0.80 M, 0.85 M, 0.90 M, or 0.95 M.

In one embodiment, liquid compositions, such as aqueous solutions, have a permeant ion concentration from about 30 mM to about 300 mM. In another embodiment, the permeant ion concentration is between 50 mM and 200 mM. In another embodiment, the permeant ion is selected from the list consisting of chloride and bromide. In another embodiment the permeant ion is chloride. In another embodiment, the permeant ion is bromide.

In some embodiments, aqueous solution compositions comprise a buffer. For example, in some embodiments, the solution comprises acetate. In some embodiments, aqueous solution compositions comprise a base such as NaOH. In some embodiments, aqueous solution compositions comprise an acid such as HCl.

It is contemplated that in some embodiments, reconstituted solutions may be stored in a reconstituted state at room temperature prior to further dilution for injection or topical administration. In some embodiments, storage times at room temperature after reconstitution are much longer than current compositions. In some embodiments, admixing can occur, for example, in an intravenous bag. To prepare an admixture, sufficient reconstituted solution is mixed in an intravenous bag containing a pharmaceutically acceptable diluent such as saline or dextrose solution such as 5DW.

The concentration of admixtures may easily be determined by those of ordinary skill in the art. The time available for admixture of reconstituted solutions from the compositions may be much longer than those of previously described formulations. Storage times of the admixtures at room temperature may also be much longer than those of the existing compositions. Once admixed, the tetracycline solution is ready for administration by or to the patient. The admixture may be administered alone or together with another pharmaceutical agent or composition.

In some embodiments, the composition does not comprise a pharmaceutically acceptable oil. In some embodiments, an oil can refer to a hydrocarbon compound that is liquid at room temperature and insoluble in water. Examples of pharmaceutically acceptable oils include polyoxyethylene hydrogenated castor oils such as PEG-40 hydrogenated castor oil and PEG-50 hydrogenated castor oil. More examples of pharmaceutically acceptable oils include olive oil, sesame oil, soybean oil, safflower oil, cottonseed oil, corn oil, sunflower oil, arachis oil, coconut oil, an omega-3 polyunsaturated oil, and an omega-3 marine triglyceride.

In some embodiments, the composition does not comprise a pyridine-containing compound. In one embodiment, the pyridine-containing compound is nicotinamide.

Although some embodiments include gluconate (e.g., as the gluconate salt of a divalent or trivalent metal cation), other embodiments include compositions that do not comprise gluconate.

In some embodiments, the composition does not comprise a non-aqueous tetracycline-solubilizing co-solvent. Such solubilizing co-solvents can include the oil, pyridine-containing compound, and gluconate described above.

Although some embodiments include an antioxidant, other embodiments include compositions that do not comprise an antioxidant (e.g., sodium or magnesium formaldehyde sulfoxylate; sodium sulfite, metabisulfite or bisulfite; sodium sulfide; alpha-monothioglycerol (also referred to as thioglycerol); and thiosorbitol).

Other various embodiments include compositions that do not include one or more of an alcohol (e.g., a polyhydric alcohol, such as, propylene glycol, ethylene glycol), glycerol, polyethylene glycol, a pyrrolidone-containing compound, a water-miscible local anaesthetic (e.g., procaine, tetracaine), urea, lactose, or a dehydrating agent (e.g., ethyl acetate, acetic anhydride, absolute ethanol, ethyl acetate, acetic anhydride, and mixtures thereof).

Some embodiments include compositions comprising a 7-dimethylamino-tetracycline and a cation. In some such embodiments the 7-dimethylamino-tetracycline is minocycline. In some embodiments, the minocycline is minocycline HCl. In some embodiments the cation comprises $Mg^{2+}$. In some embodiments, the compositions include a salt selected from $MgCl_2$ (e.g., $MgCl_2.6H_2O$), $MgSO_4$ (e.g. $MgSO_4.7H_2O$) and magnesium acetate (e.g., $Mg(CH_3COO)_2.3H_2O$). In some embodiments, the molar ratio of divalent or trivalent cation to minocycline is greater than 1:1, 2:1, 3:1, 4:1, 5:1, 6:1, 7:1, 8:1, 9:1, or 10:1. In some embodiments, the molar ratio of divalent or trivalent cation to minocycline is greater than 10:1, 20:1, 30:1, 40:1, or 50:1. Some embodiments include a buffer. In some such embodiments, the buffer includes NaOH, or sodium acetate (e.g., $NaCH_3COO.3H_2O$).

Some compositions comprise minocycline and $MgCl_2.6H_2O$ with a Mg to minocycline molar ratio of about 5:1 in a base comprising NaOH. Some such embodiments are suitable for intravenous use.

Some compositions comprise minocycline and $MgSO_4.7H_2O$ with a Mg to minocycline molar ratio of about 5:1 in a buffer comprising $NaCH_3COO.3H_2O$ with a pH in the range 4.5-5.5 and an osmolality in the range of about 275-375 mOsm/kg. Some such compositions can be prepared as an aqueous solution and lyophilized. As will be understood by a skilled artisan, the pH and osmolality of a reconstituted solution can have a pH in the range 4.5-5.5 and an osmolality in the range of about 275-375 mOsm/kg. Some such embodiments are suitable for intravenous use.

Some embodiments comprise minocycline and $Mg(CH_3COO)_2.3H_2O$ with a Mg to minocycline molar ratio of about 5:1 with no buffer added. Some such embodiments are suitable for intravenous use.

Some embodiments include minocycline and $MgSO_4.7H_2O$ with a Mg to minocycline molar ratio of about 5:1 in a base comprising NaOH with a pH in the range 5.5-6.5. Some such compositions can be prepared as an aqueous solution and lyophilized. As will be understood by a skilled artisan, the pH of a reconstituted solution can have a pH in the range 5.5-6.5. Some such embodiments are suitable for intravenous use.

Some embodiments comprise tigecycline and MgSO$_4$.7H$_2$O with a Mg to minocycline molar ratio of about 5:1 in a buffer comprising NaOH with a pH in the range 5.5-6.5. Some embodiments comprise tigecycline and MgSO$_4$.7H$_2$O with a Mg to minocycline molar ratio of about 12:1 in a base comprising NaOH with a pH in the range 5.5-6.5. Some such compositions can be prepared as an aqueous solution and lyophilized. As will be understood by a skilled artisan, the pH of a reconstituted solution can have a pH in the range 5.5-6.5. Some such embodiments are suitable for intravenous use.

Some embodiments comprise tigecycline and MgCl$_2$.6H$_2$O with a Mg to minocycline molar ratio of about 5:1 in a buffer comprising NaOH with a pH in the range 5.5-6.5. Some embodiments comprise tigecycline and MgCl$_2$.6H$_2$O with a Mg to minocycline molar ratio of about 12:1 in a base comprising NaOH with a pH in the range 5.5-6.5. Some such compositions can be prepared as an aqueous solution and lyophilized. As will be understood by a skilled artisan, the pH of a reconstituted solution can have a pH in the range 5.5-6.5. Some such embodiments are suitable for intravenous use.

Some embodiments comprise tigecycline and MgSO$_4$.7H$_2$O with a Mg to minocycline molar ratio of about 5:1 in a buffer comprising NaOH with a pH in the range 6.0-7.0. Some embodiments comprise tigecycline and MgSO$_4$.7H$_2$O with a Mg to minocycline molar ratio of about 12:1 in a base comprising NaOH with a pH in the range 6.0-7.0. Some such compositions can be prepared as an aqueous solution and lyophilized. As will be understood by a skilled artisan, the pH of a reconstituted solution can have a pH in the range 6.0-7.0. Some such embodiments are suitable for topical use. Some such compositions comprise tigecycline with greater than 90%, 95%, or 98% stability for at least 30 days. Some embodiments include compositions comprising an additional constituent such as benzalkonium chloride, a steroid such as hydrocortisone, dexamethasone, thonzonium bromide, tyloxapol, an antiseptic agent such as boric acid, a preservative such as benzalkonium chloride.

Some embodiments comprise tigecycline and CaCl$_2$.6H$_2$O with a Ca:minocycline:molar ratio of about 5:1 in a base comprising NaOH with a pH in the range 6.0-7.0. Some embodiments comprise tigecycline and CaCl$_2$.6H$_2$O with a Ca to tigecycline molar ratio of about 12:1 in a base comprising NaOH with a pH in the range 6.0-7.0. Some such compositions can be prepared as an aqueous solution and lyophilized. As will be understood by a skilled artisan, the pH of a reconstituted solution can have a pH in the range 6.0-7.0. Some such embodiments are suitable for topical use. Some such compositions comprise tigecycline with greater than 90%, 95%, 98% stability for at least 30 days. Some embodiments include compositions comprising an additional constituent such as benzalkonium chloride, a steroid such as hydrocortisone, dexamethasone, thonzonium bromide, tyloxapol, an antiseptic agent such as boric acid, a preservative such as benzalkonium chloride.

Some embodiments include pharmaceutical compositions comprising an aqueous solution of minocycline and a divalent or trivalent cation, wherein the molar ratio of divalent or trivalent cation to minocycline is greater than 2:1. In some embodiments, the molar ratio of divalent or trivalent cation to minocycline is greater than about 3:1, greater than about 5:1, greater than about 8:1, greater than about 10:1. In some embodiments, the divalent or trivalent cation is selected from iron, copper, zinc, manganese, nickel, cobalt, aluminum, calcium, magnesium and gallium. In particular embodiments, the divalent or trivalent cation is selected from magnesium, calcium, and zinc. In some embodiments, the solution comprises magnesium sulfate and/or magnesium oxide. In particular embodiments, the composition is suitable for intravenous administration.

More embodiments include a pharmaceutical composition comprising an aqueous solution of an 7-dimethylamino-tetracycline antibiotic and a divalent or trivalent cation, wherein the molar ratio of divalent or trivalent cation to tetracycline antibiotic is greater than 3:1 and wherein the solution does not comprise an oil, gluconate, or a pyridine-containing compound, has a pH greater than 2 and less than 7, and is suitable for intravenous administration. In some embodiments, the 7-dimethylamino-tetracycline is selected from minocycline, PTK796, and glycylcyclines (e.g. tigecycline).

Some embodiments include a water-soluble solid composition, comprising minocycline or a salt thereof and a salt that comprises a divalent or trivalent cation. In some embodiments, the molar ratio of divalent or trivalent cation to minocycline is greater than about 1:1, greater than about 2:1, greater than about 3:1, greater than about 5:1, greater than about 8:1, greater than about 10:1. In some embodiments, the salt is selected from magnesium chloride, magnesium bromide, magnesium sulfate, calcium chloride, calcium bromide, calcium sulfate, zinc chloride, gallium chloride, magnesium malate, magnesium gluconate, magnesium citrate, calcium gluconate, calcium citrate, zinc gluconate, zinc acetate, and zinc citrate. In preferred embodiments, the salt is magnesium sulfate. In some embodiments, the composition comprises sodium acetate. In certain embodiments, the composition does not comprise an antioxidant, a pyridine-containing compound (e.g., nicotinamide), or gluconate.

More embodiments include water-soluble solid compositions comprising a 7-dimethylamino-tetracycline antibiotic and a salt comprising a divalent or trivalent cation, wherein the molar ratio of divalent or trivalent cation to tetracycline antibiotic is greater than 3:1 and wherein the composition does not comprise gluconate or a pyridine-containing compound. In some embodiments, the 7-dimethylamino-tetracycline is selected from minocycline, glycylcyclines (e.g. tigecycline) and PTK796.

In some embodiments, the water-soluble compositions described above are in the form of a lyophile.

Methods of Preparation

Some embodiments of the present invention include methods for preparing the compositions described herein. Some such methods include combining a tetracycline antibiotic and a divalent or trivalent cation. Some methods further comprise modifying the pH of the compositions. In some methods, modifying the pH comprises adjusting the pH with a pH modifying agent. Examples of pH modifying agents include hydrochloric acid, gentisic acid, lactic acid, citric acid, acetic acid, phosphoric acid, sodium hydroxide, sodium bicarbonate and sodium carbonate. In some embodiments, the pH-modifying agent includes any pharmaceutically acceptable acid, base or buffer capable of adjusting the pH of a tetracycline antibiotic/metal cation solution to between about 3.0 to about 7.0, about 4.0 to about 5.0, about 5.0 to 6.0, about 5.5 to 6.5, about 6.0 to 6.5 or about 4.2 to 4.8. In some embodiments, the acid, base or buffer is used to adjust the pH of a tetracycline antibiotic/metal cation solution to a pH less than 7, 6, 5, or 4. In some embodiments, the acid, base or buffer is used to adjust the pH of a tetracycline antibiotic/metal cation solution to a pH greater than 2 and less than 7, greater than 4 and less than 7, greater than 4 and less than 6, and greater than 4 and less than 5. Examples of such acids include but are not limited to hydrochloric acid, including 1.0 N HCl, gentisic acid, lactic acid, citric acid, acetic acid and phosphoric acid. Examples of suitable buffers include as components succinates and acetate. Examples of such bases include but are not limited to aqueous solutions of sodium hydroxide, including 1.0 N NaOH solution, sodium bicarbonate and sodium carbonate.

Compositions of the invention may be prepared via a number of acceptable methods. For example, the metal salts are dissolved in water and the tetracycline antibiotic is added to this solution. Alternatively, the antibiotic is dissolved first and the metal salt is added to the solution. The pH of the solution is then adjusted with an acid, a base or buffer. Other optional agents such as an antioxidant or carbohydrate are then dissolved in the solution. The final solution may be then be used directly in therapy or lyophilized to dryness to form a lyophilized powder or cake for later reconstitution.

In another example, a tetracycline antibiotic may be dry blended with the metal salts and other optional ingredients, and the residual mixture dissolved in water. After the pH of the solution is adjusted, the solution may then be used in therapy or lyophilized to dryness to form a powder or cake.

Lyophilization of solutions described herein may be accomplished by any pharmaceutically acceptable means. Once lyophilized, the compositions of the invention may be stored under an inert gas, such as nitrogen, to further slow the degradation process.

The tetracycline antibiotic used in the various preparation techniques may be any solid-state form of the tetracycline that is sufficiently soluble in water. Such solid-state forms include crystalline tetracycline polymorphs, amorphous forms and salts.

One embodiment for preparing a minocycline-containing pharmaceutical composition includes dissolving minocycline and a salt that comprises a divalent of trivalent cation in water to form a solution and adjusting the pH of the solution to be less than about 7, less than about 6, less than about 5, less than about 4, or less than about 3. In some embodiments, the pH of the solution is adjusted to be greater than about 2 and less than about 7, greater than about 4 and less than about 7, or greater than about 4 and less than about 6. In some embodiments, adjusting the pH comprises adding a base, e.g., NaOH. In some embodiments, adjusting the pH comprises forming a buffer. In some embodiments, forming the buffer comprises adding sodium acetate.

More embodiments for methods of preparing a minocycline-containing pharmaceutical composition includes dissolving minocycline in a solution comprising a divalent or trivalent cation; and adjusting the pH of the solution to be less than 7.

In some embodiments, a solution of a 7-dimethylamino-tetracycline can be prepared by adding a 7-dimethylamino-tetracycline, an aqueous solution of divalent or trivalent salt to provide a certain divalent or trivalent salt to 7-dimethyl-amino-tetracycline molar ratio. The pH of the solution can be adjusted to a certain pH with a buffer, acid, or a base. The osmolality of the solution can be adjusted to a certain osmolality. The solution can be lyophilized. The lyophilized solution can be reconstituted with a diluent such as water.

In some embodiments, a solution of a 7-dimethylamino-tetracycline can be prepared by adding a 7-dimethylamino-tetracycline to an acid, such as HCl. The solution can be lyophilized. The lyophilized solution can be reconstituted with a diluent comprising a divalent or trivalent salt to provide a certain divalent or trivalent salt to 7-dimethyl-amino-tetracycline molar ratio. The diluent can further comprise an acid, base, or buffer, such as sodium acetate, to provide a solution of a certain pH.

In some embodiments, minocycline can be in a buffer comprising $MgSO_4$ at pH 5. The solution can be lyophilized. The lyophilisate can be reconstituted in an aqueous diluent. In some embodiments, minocycline can be solubilized in an aqueous solution comprising HCl, MgSO4 and sodium acetate. The solution can be lyophilized. In some embodiments, minocycline can be solubilized in an aqueous solution comprising HCl. The solution can be lyophilized. The lyophilisate can be reconstituted in an aqueous solution. In some embodiments, the reconstituting solution can lack Mg.

Kits

Some embodiments of the present invention include kits comprising a composition described herein. Some kits include a single use container comprising a composition described herein. Single use containers include ampules, vials, and the like. The single-use container can comprise a lyophilized formulation of a composition described herein. Some kits include a diluent for reconstituting the lyophilized formulations of a composition or pharmaceutical composition described herein.

In some embodiments, the compositions of the invention may be prepared for single-dosage use. In this embodiment, the solutions of the invention are lyophilized in individual vials such as 20-mL vials. Upon lyophilization, the vials are stoppered with any acceptable stopper. The stoppered vials are then shipped for use. When needed, the vials can be reconstituted by adding sufficient diluents to achieve the desired concentration of tetracycline. The concentration of reconstituted solutions may be easily determined by those of ordinary skill in the art. Any pharmaceutically acceptable diluent may be used. Examples of such diluents include but are not limited to water, 0.9% saline, Lactated Ringer's injection solution and dextrose solutions including 5% dextrose (5DW).

In some embodiments, the diluent does not comprise a pharmaceutically acceptable oil (e.g., polyoxyethylene hydrogenated castor oils), a pyridine-containing compound (e.g., nicotinamide), gluconate, an antioxidant, an alcohol (e.g., a polyhydric alcohol, such as, propylene glycol, ethylene glycol), glycerol, polyethylene glycol, a pyrrolidone-containing compound, a water-miscible local anaesthetic (e.g., procaine, tetracaine), urea, lactose, or a dehydrating agent (e.g., ethyl acetate, acetic anhydride, absolute ethanol, ethyl acetate, acetic anhydride, and mixtures thereof). In some embodiments, the diluent does not comprise a tetracycline-solubilizing cosolvent.

In some embodiments, the diluent contains the divalent or trivalent cation. For example, some embodiments include kits that comprise a first container comprising a diluent that comprises an aqueous solution of a divalent or trivalent cation; and a second container comprising a solid composition soluble in the diluent, wherein the solid composition comprises minocycline in an amount such that the molar ratio of the divalent or trivalent cation to minocycline is greater than about 2:1. In some embodiments, the diluent comprises an acid, e.g., HCl. In some embodiments, the diluent comprises a buffer. In some embodiments, the buffer is sodium acetate.

More embodiments include kits comprising a first container comprising a diluent that comprises an aqueous solution of a divalent or trivalent cation; and a second container comprising a solid composition soluble in the diluent, wherein the solid composition comprises a tetracycline antibiotic in an amount such that the molar ratio of the divalent or trivalent cation to tetracycline antibiotic is greater than 3:1.

More embodiments include single use vials comprising any composition wherein the vial comprises an amount of a tetracycline of at least 100 µg, 200 µg, 300 µg, 400 µg, 500 µg, 600 µg, 700 µg, 800 µg, 900 µg, 1000 µg. In some embodiments, the vial comprises an amount of a tetracycline of at least 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, and 130 mg. In some embodiments, the vial comprises an amount of a tetracycline of at least 100 mg, 200 mg, 300 mg, 400 mg, and 500 mg. In some embodiments, the vial comprises about 100 mg of a tetracycline. In some embodiments, the tetracycline is minocycline. In some embodiments, the tetracycline is tigecycline. In some such embodiments, a vial can comprise greater than 30 mg and less than 100 mg tigecycline.

Methods of Treatment

Some embodiments include methods of treating or preventing a bacterial infection in a subject by administering a composition described herein. "Treating," as used herein, refers to administering a pharmaceutical composition for therapeutic purposes to a patient suffering from a bacterial infection. "Preventing," as used herein, refers to treating a patient who is not yet infected, but who is susceptible to, or otherwise at risk of, a particular infection, whereby the treatment reduces the likelihood that the patient will develop an infection.

In some embodiments, the administration is via an intravenous route such as by administering an aqueous solution described herein intravenously.

Some such methods include administering an aqueous solution of minocycline and a divalent or trivalent cation to a subject via an intravenous route. Such solutions are described herein.

Some embodiments include administering an aqueous solution of a 7-dimethylamino-tetracycline antibiotic and a divalent or trivalent cation to a subject via an intravenous route, wherein the molar ratio of divalent or trivalent cation to tetracycline antibiotic is greater than about 3:1 and wherein the solution does not comprise gluconate or a pyridine-containing compound and has a pH greater than 2 and less than 7.

In some embodiments of intravenous administration, the compositions described herein permit use of lower volumes and faster infusion times due to increased concentrations of tetracycline antibiotic and reduced injection site phlebitis as compared to currently available intravenous formulations. In some embodiments, the total volume administered is less than 50 ml, less than 60 ml, less than 70 ml, less than 80 ml, less than 90 ml, less than 100 ml, less than 110 ml, less than 120 ml, less than 130 ml, less than 140 ml, less than 150 ml, less than 200 ml, less than 300 ml, less than 400 ml, less than 500 ml, or less than 1000 ml. In some embodiments, about 100 ml is administered. In some embodiments, the entire volume to be administered is administered in less than 10 minutes, less than 20 minutes, less than 30 minutes, less than 40 minutes, less than 50 minutes, less than 60 minutes, less than 70 minutes, less than 80 minutes, less than 90 minutes, less than 2 hours, less than 3 hours, or less than 4 hours. In some embodiments, the entire volume is administered in 20-70 minutes. In some embodiments, the entire volume is administered in 30-60 minutes.

Some embodiments include administering a composition described herein by a topical route. Examples of topical routes include skin, eye, ear, rectal, vaginal, urethral. Methods of such administration are well known in the art and can include aqueous solution, spray, suppository, salve, or an ointment or the like. Accordingly, some embodiments include administering an aqueous solution of a 7-dimethylamino-tetracycline antibiotic and a divalent or trivalent cation to a subject via a topical route. In some such embodiments, the molar ratio of divalent or trivalent cation to tetracycline antibiotic is greater than about 3:1. In some embodiments, the solution does not comprise gluconate or a pyridine-containing compound. In some embodiments, the solution has a pH greater than 2 and less than 7.

Other embodiments include administering a composition described herein by pulmonary inhalation. For example, compositions may be administered by inhalation of an aerosol of the composition. The aerosol may be formed using dry particles of the composition or by nebulization of a solution of suspension of the composition. Any suitable aerosolization device may be used, including dry-powder inhalers, metered-dose inhalers, and nebulizers.

The following examples illustrate various embodiments of the invention and are not intended to limit the invention in any way.

EXAMPLES

Example 1

Stability at 37° C. for Solutions of Tigecycline or Tygacil® Containing Metal Cations General procedures: Some of following examples include experiments in which the stabilities of various aqueous solutions of a tetracycline were analyzed. Some solutions included a carbohydrate and/or various molar amounts of metal salts.

The pH of the solutions were adjusted with hydrochloric acid or sodium hydroxide solution. The solutions were incubated at room temperature (approximately 22° C.) or at 37° C. Incubation of solutions at 37° C. was used as a model for long-term storage of solutions.

The stabilities of various aqueous solutions of a tetracycline were analyzed using HPLC. HPLC analyses were conducted on an Agilent 1200: Column: Eclipse Plus C18 4.6×150 mm, 5 µm. Detection: UV at 248 nm. Flow rate: 1.2 mL/min. Tigecycline retention time=4.30 min. Gradient: Solvent A=0.1% trifluoroacetic acid in acetonitrile. Solvent B=0.1% trifluroacetic acid in water. TABLE 1 shows the HPLC gradient used.

TABLE 1

| Time (min) | % Solvent A | % Solvent B |
|---|---|---|
| 0.0 | 5 | 95 |
| 9.5 | 50 | 50 |
| 10.0 | 5 | 95 |
| 15.0 | 5 | 95 |

A 10 mg/mL Tigecycline aqueous solution was prepared and 300 µL aliquots dispensed into polypropylene tubes. The volume of each tube was adjusted to 1 ml with various dilutions of 0.1 M $MgCl_2$, 0.1 M $CaCl_2$ or 0.1 M $ZnCl_2$ to achieve the desired molar ratio of Tigecycline:metal cation.

The tubes were incubated in the dark at 37° C. Samples of each solution were taken at various time points and analyzed by HPLC. The fraction of remaining Tigecycline in each sample was determined.

A 10 mg/mL (17.08 mol/L) aqueous solution of Tygacil® (Lot D 90293, 53 mg), a commercial Tigecycline formulation containing lactose, was prepared, and 240 µL aliquots were dispensed into polypropylene tubes. The volume of each tube was adjusted to 1 ml with various dilutions of 0.1 M $MgCl_2$, 0.1 M $CaCl_2$ or 0.1 M $ZnCl_2$ to achieve the desired molar ratio of Tigecycline:metal cation. The tubes containing the solution were incubated in the dark at 37° C. Samples of each solution were taken at various time points and analyzed by HPLC. The fraction of remaining Tigecycline in each sample was determined.

The percentages of Tigecycline remaining at Day 0, 1, 2, 5, and 7 for solutions of Tigecycline at various molar ratios with $MgCl_2$, $CaCl_2$, or $ZnCl_2$ are shown in TABLE 2, TABLE 3, and TABLE 4, respectively. The percentages of Tigecycline remaining at Day 0, 1, 2, 5, and 7 for solutions of Tygacil® at various ratios with $MgCl_2$, $CaCl_2$, or $ZnCl_2$ are shown in TABLE 5, TABLE 6, and TABLE 7, respectively.

TABLE 2

| $MgCl_2$:Tigecycline Molar ratio | Day 0 | Day 1 | Day 2 | Day 5 | Day 7 |
| --- | --- | --- | --- | --- | --- |
| 10:1 | 99.42 | 98.93 | 97.68 | 92.31 | 85.95 |
| 5:1 | 99.45 | 98.85 | 97.30 | 88.64 | 81.41 |
| 2:1 | 99.50 | 98.57 | 96.85 | 84.95 | 73.95 |
| 1:1 | 99.64 | 98.64 | 96.70 | 82.54 | 67.87 |
| 0.5:1 | 99.60 | 98.45 | 96.52 | 79.39 | 62.20 |
| 0.2:1 | 99.56 | 98.44 | 95.91 | 72.81 | 53.83 |
| 0.1:1 | 99.50 | 98.29 | 95.66 | 67.28 | 48.68 |
| 0:1 | 99.53 | 98.23 | 95.18 | 58.42 | 40.90 |

TABLE 3

| $CaCl_2$:Tigecycline Molar ratio | Day 0 | Day 1 | Day 2 | Day 5 | Day 7 |
| --- | --- | --- | --- | --- | --- |
| 10:1 | 99.49 | 99.02 | 97.89 | 91.88 | 86.31 |
| 5:1 | 99.44 | 98.66 | 97.31 | 87.13 | 80.87 |
| 2:1 | 99.38 | 98.06 | 96.66 | 83.63 | 75.05 |
| 1:1 | 99.58 | 98.33 | 96.54 | 81.30 | 70.18 |
| 0.5:1 | 99.56 | 98.61 | 96.15 | 76.00 | 64.81 |
| 0.2:1 | 99.58 | 98.47 | 95.99 | 72.84 | 57.19 |
| 0.1:1 | 99.56 | 98.32 | 95.66 | 67.89 | 49.75 |
| 0:1 | 99.49 | 98.17 | 94.98 | 59.11 | 39.31 |

TABLE 4

| $ZnCl_2$:Tigecycline Molar ratio | Day 0 | Day 1 | Day 2 | Day 5 | Day 7 |
| --- | --- | --- | --- | --- | --- |
| 10:1 | 99.15 | 99.01 | 97.82 | 96.65 | 95.41 |
| 5:1 | 99.21 | 98.66 | 97.76 | 95.81 | 92.85 |
| 2:1 | 99.31 | 98.46 | 97.32 | 91.02 | 85.64 |
| 1:1 | 99.54 | 98.66 | 97.59 | 91.27 | 82.49 |
| 0.5:1 | 99.53 | 98.66 | 97.21 | 87.15 | 76.43 |
| 0.2:1 | 99.52 | 98.38 | 95.95 | 79.08 | 66.83 |
| 0.1:1 | 99.50 | 98.39 | 96.11 | 78.80 | 64.93 |
| 0:1 | 99.46 | 98.37 | 95.02 | 56.30 | 39.05 |

TABLE 5

| $MgCl_2$:Tygacil® Molar ratio | Day 0 | Day 1 | Day 2 | Day 5 | Day 7 |
| --- | --- | --- | --- | --- | --- |
| 10:1 | 99.61 | 99.38 | 98.97 | 96.51 | 93.52 |
| 5:1 | 99.47 | 99.46 | 98.83 | 95.38 | 90.55 |
| 2:1 | 99.49 | 99.32 | 98.72 | 93.20 | 84.03 |
| 1:1 | 99.63 | 99.38 | 98.55 | 89.21 | 74.30 |
| 0.5:1 | 99.59 | 99.28 | 98.36 | 86.97 | 68.84 |
| 0.2:1 | 99.54 | 99.26 | 98.43 | 86.41 | 64.91 |
| 0.1:1 | 99.48 | 99.19 | 98.19 | 72.43 | 44.71 |

TABLE 6

| $CaCl_2$:Tygacil® Molar ratio | Day 0 | Day 1 | Day 2 | Day 5 | Day 7 |
| --- | --- | --- | --- | --- | --- |
| 10:1 | 99.41 | 99.41 | 98.88 | 96.51 | 89.98 |
| 5:1 | 99.40 | 99.29 | 98.48 | 95.38 | 85.50 |
| 2:1 | 99.45 | 99.22 | 98.34 | 93.20 | 79.62 |
| 1:1 | 99.71 | 99.44 | 98.44 | 89.21 | 75.34 |
| 0.5:1 | 99.53 | 99.16 | 98.32 | 86.97 | 70.45 |
| 0.2:1 | 99.54 | 99.21 | 98.30 | 86.41 | 63.78 |
| 0:1 | 99.47 | 99.16 | 98.16 | 72.43 | 42.88 |

TABLE 7

| $ZnCl_2$:Tygacil® Molar ratio | Day 0 | Day 1 | Day 2 | Day 5 | Day 7 |
| --- | --- | --- | --- | --- | --- |
| 10:1 | 99.41 | 99.45 | 98.90 | 97.89 | 95.78 |
| 5:1 | 99.44 | 99.27 | 98.68 | 96.87 | 94.30 |
| 2:1 | 99.39 | 99.25 | 98.74 | 96.09 | 92.22 |
| 1:1 | 99.56 | 99.50 | 98.98 | 95.60 | 90.67 |
| 0.5:1 | 99.48 | 99.25 | 98.78 | 93.73 | 86.02 |
| 0.2:1 | 99.52 | 99.35 | 98.43 | 89.34 | 77.79 |
| 0:1 | 99.50 | 99.27 | 98.12 | 69.85 | 42.15 |

While Tigecycline decomposed in all tubes over 7 days, the rate of decomposition was significantly lower in solutions containing higher molar ratios of metal cation. The rates of Tigecycline decomposition in the presence of calcium or magnesium cations were similar; however, the rate of Tigecycline decomposition in the presence of zinc was significantly lower. The presence of lactose in the Tygacil® formulation further decreased the rate of decomposition.

Example 2

Stability at Room Temperature for Solutions of Tigecycline or Tygacil® Containing Metal Cations A 10 mg/mL Tigecycline aqueous solution was prepared and 240 µL aliquots dispensed into polypropylene tubes. The volume of each tube was adjusted to 1 ml with various dilutions of 0.1 M $MgCl_2$, 0.1 M $CaCl_2$ or 0.1 M $ZnCl_2$ to achieve the desired molar ratio of Tigecycline:metal cation. The tubes were incubated in the dark at 37° C. Samples of each solution were taken at various time points and analyzed by HPLC. The fraction of remaining Tigecycline in each sample was determined.

A 10 mg/mL aqueous solution of Tygacil® (Lot D 90293, 53 mg) was prepared, and 240 µL aliquots were dispensed into polypropylene tubes. The volume of each tube was adjusted to 1 ml with various dilutions of 0.1 M $MgCl_2$, 0.1 M $CaCl_2$ or 0.1 M $ZnCl_2$ to achieve the desired molar ratio of Tigecycline:metal cation. The tubes were incubated in the dark at 37° C. Samples of each solution were taken at various time points and analyzed by HPLC. The fraction of remaining Tigecycline in each sample was determined.

The percentages of Tigecycline remaining at Day 0, 1, 2, 5, 7, 14, 21, 28, and 36 for solutions of Tigecycline at various molar ratios with MgCl$_2$, CaCl$_2$, or ZnCl$_2$ are shown in TABLE 8, TABLE 9, and TABLE 10, respectively. The percentages of Tigecycline remaining at Day 0, 1, 2, 5, 7, 14, 21, 28, and 36 for solutions of Tygacil® at various ratios with MgCl$_2$, CaCl$_2$, or ZnCl$_2$ are shown in TABLE 11, TABLE 12, and TABLE 13, respectively.

TABLE 8

| MgCl$_2$:Tigecycline Molar ratio | Day 0 | Day 1 | Day 2 | Day 5 | Day 7 | Day 14 | Day 21 | Day 28 | Day 36 |
|---|---|---|---|---|---|---|---|---|---|
| 10:1 | 99.58 | 99.32 | 99.46 | 99.03 | 98.62 | 95.52 | 91.90 | 85.33 | 76.89 |
| 5:1 | 99.45 | 99.32 | 99.41 | 98.74 | 98.16 | 94.04 | 87.10 | 76.71 | 62.60 |
| 2:1 | 99.51 | 99.27 | 99.43 | 98.46 | 96.97 | 89.87 | 76.29 | 58.07 | 40.67 |
| 1:1 | 99.66 | 99.45 | 99.36 | 98.35 | 96.49 | 85.88 | 66.59 | 46.07 | 31.90 |
| 0.5:1 | 99.64 | 99.40 | 99.35 | 97.76 | 96.16 | 81.98 | 59.70 | 39.79 | 28.16 |
| 0.2:1 | 99.56 | 99.37 | 99.28 | 97.93 | 95.45 | 75.81 | 50.38 | 34.00 | 24.19 |
| 0:1 | 99.46 | 99.24 | 99.15 | 97.01 | 94.08 | 61.98 | 38.99 | 24.55 | 16.33 |

TABLE 9

| CaCl$_2$:Tigecycline Molar ratio | Day 0 | Day 1 | Day 2 | Day 5 | Day 7 | Day 14 | Day 21 | Day 28 | Day 36 |
|---|---|---|---|---|---|---|---|---|---|
| 10:1 | 99.58 | 99.34 | 99.41 | 99.05 | 98.59 | 95.45 | 92.00 | 86.92 | 82.47 |
| 5:1 | 99.48 | 99.25 | 99.27 | 98.66 | 98.13 | 93.61 | 88.60 | 81.75 | 74.95 |
| 2:1 | 99.37 | 99.27 | 99.25 | 98.03 | 97.16 | 91.36 | 82.92 | 72.83 | 62.43 |
| 1:1 | 99.57 | 99.38 | 99.30 | 98.53 | 96.92 | 89.14 | 78.35 | 65.46 | 53.22 |
| 0.5:1 | 99.59 | 99.30 | 99.30 | 98.32 | 96.54 | 86.26 | 72.73 | 58.20 | 45.11 |
| 0.2:1 | 99.48 | 99.32 | 99.27 | 97.94 | 95.75 | 80.39 | 61.83 | 45.47 | 26.69 |
| 0:1 | 99.44 | 99.29 | 99.17 | 96.76 | 93.75 | 60.72 | 38.08 | 23.94 | 15.72 |

TABLE 10

| ZnCl$_2$:Tigecycline Molar ratio | Day 0 | Day 1 | Day 2 | Day 5 | Day 7 | Day 14 | Day 21 | Day 28 | Day 36 |
|---|---|---|---|---|---|---|---|---|---|
| 10:1 | 99.24 | 98.99 | 99.49 | 99.30 | 99.19 | 97.49 | 97.63 | 96.09 | 94.32 |
| 5:1 | 99.29 | 99.13 | 99.05 | 99.27 | 99.16 | 97.40 | 95.98 | 92.80 | 90.60 |
| 2:1 | 99.34 | 99.23 | 99.51 | 99.06 | 98.82 | 95.79 | 93.63 | 86.84 | 80.66 |
| 1:1 | 99.53 | 99.39 | 99.47 | 99.03 | 98.48 | 94.61 | 88.48 | 79.03 | 69.44 |
| 0.5:1 | 99.50 | 99.39 | 99.33 | 98.76 | 96.77 | 90.07 | 78.03 | 65.63 | 54.07 |
| 0.2:1 | 99.46 | 99.37 | 99.33 | 98.24 | 96.50 | 85.72 | 69.89 | 55.13 | 41.97 |
| 0:1 | 99.44 | 99.39 | 99.12 | 97.28 | 93.31 | 59.45 | 37.09 | 23.57 | 15.48 |

TABLE 11

| MgCl$_2$:Tygacil® Molar ratio | Day 0 | Day 1 | Day 2 | Day 5 | Day 7 | Day 14 | Day 21 | Day 28 | Day 36 |
|---|---|---|---|---|---|---|---|---|---|
| 10:1 | 99.44 | 99.53 | 99.34 | 99.25 | 99.07 | 97.30 | 95.37 | 92.20 | 86.32 |
| 5:1 | 99.44 | 99.61 | 99.60 | 99.45 | 99.32 | 97.66 | 95.34 | 90.98 | 83.58 |
| 2:1 | 99.48 | 99.63 | 99.56 | 99.43 | 99.19 | 96.67 | 91.94 | 81.95 | 66.57 |
| 1:1 | 99.55 | 99.62 | 99.61 | 99.09 | 99.11 | 96.50 | 89.71 | 74.36 | 55.95 |
| 0.5:1 | 99.49 | 99.64 | 99.60 | 99.33 | 98.70 | 95.10 | 84.39 | 64.70 | 45.04 |
| 0.2:1 | 99.49 | 99.63 | 99.57 | 99.28 | 98.89 | 94.03 | 79.53 | 57.09 | 37.94 |
| 0:1 | 99.44 | 99.57 | 99.57 | 99.25 | 98.78 | 89.19 | 65.09 | 42.56 | 28.38 |

TABLE 12

| CaCl$_2$:Tygacil® Molar ratio | Day 0 | Day 1 | Day 2 | Day 5 | Day 7 | Day 14 | Day 21 | Day 28 | Day 36 |
|---|---|---|---|---|---|---|---|---|---|
| 10:1 | 99.32 | 99.51 | 99.45 | 99.50 | 99.26 | 97.41 | 95.08 | 92.06 | 87.88 |
| 5:1 | 99.35 | 99.51 | — | 99.33 | 99.02 | 97.36 | 93.42 | 88.57 | 82.75 |
| 2:1 | 99.40 | 99.67 | 99.46 | 99.25 | 98.97 | 95.76 | 90.00 | 81.77 | 72.75 |
| 1:1 | 99.49 | 99.60 | 99.54 | 99.39 | 99.02 | 95.44 | 88.25 | 77.42 | 65.65 |
| 0.5:1 | 99.48 | 99.60 | 99.49 | 99.30 | 98.55 | 94.80 | 85.57 | 71.96 | 58.07 |
| 0.2:1 | 99.44 | 99.57 | 99.53 | 99.27 | 98.89 | 92.70 | 80.03 | 62.28 | 47.05 |
| 0:1 | 99.45 | 99.60 | 99.55 | 99.18 | 98.70 | 88.02 | 63.58 | 40.77 | 28.00 |

TABLE 13

| ZnCl$_2$:Tygacil® Molar ratio | Day 0 | Day 1 | Day 2 | Day 5 | Day 7 | Day 14 | Day 21 | Day 28 | Day 36 |
|---|---|---|---|---|---|---|---|---|---|
| 10:1 | 98.91 | 99.49 | 99.43 | 99.46 | 99.47 | 98.98 | 98.68 | 98.17 | 98.11 |
| 5:1 | 99.15 | 99.54 | 99.51 | 99.45 | 99.35 | 98.88 | 98.26 | 97.39 | 96.15 |
| 2:1 | 99.29 | 99.57 | 99.55 | 99.35 | 99.37 | 98.60 | 97.42 | 95.30 | 92.37 |
| 1:1 | 99.44 | 99.62 | 99.55 | 99.61 | 99.33 | 97.97 | 96.29 | 92.70 | 87.08 |
| 0.5:1 | 99.47 | 99.62 | 99.59 | 99.48 | 99.25 | 97.60 | 94.10 | 86.46 | 76.49 |
| 0.2:1 | 99.45 | 99.62 | 99.61 | 99.47 | 99.19 | 96.09 | 89.52 | 77.46 | 63.06 |
| 0:1 | 99.42 | 99.54 | 99.52 | 99.14 | 98.71 | 88.25 | 64.08 | 41.19 | 28.09 |

While Tigecycline decomposed in all tubes over 36 days, the rate of decomposition was significantly lower in solutions containing higher molar ratios of metal cation. The rates of Tigecycline decomposition in the presence of calcium or magnesium cations were similar; however, the rate of Tigecycline decomposition in the presence of zinc was significantly lower. The presence of lactose in the Tygacil® formulation further decreased the rate of decomposition.

Example 3

Stability at 37° C. for Tygacil Solutions Containing High Concentrations of Metal Cations A 10 mg/mL aqueous solution of Tygacil® (Lot D 90293, 53 mg) was prepared, and 300 µL aliquots were dispensed into polypropylene tubes. The volume of each tube was adjusted to 1 ml with various dilutions of 1 M MgCl$_2$, 1 M CaCl$_2$ or 1 M ZnCl$_2$ to achieve the desired molar ratio of Tigecycline:metal cation. The tubes were incubated in the dark at 37° C. Samples of each solution were taken at various time points and analyzed by HPLC. The fraction of remaining Tigecycline in each sample was determined.

The percentages of Tigecycline remaining at Day 0, 1, 2, 5, 7, 14, and 21 for solutions of Tygacil® at various ratios with MgCl$_2$, CaCl$_2$, or ZnCl$_2$ are shown in TABLE 14, TABLE 15, and TABLE 16, respectively.

TABLE 14

| MgCl$_2$:Tygacil® Molar ratio | Day 0 | Day 1 | Day 2 | Day 5 | Day 7 | Day 14 | Day 21 |
|---|---|---|---|---|---|---|---|
| 30:1 | 99.64 | 99.59 | 99.49 | 98.54 | 97.11 | 89.62 | 77.13 |
| 20:1 | 99.61 | 99.56 | 99.23 | 97.99 | 95.94 | 85.04 | 63.47 |
| 12:1 | 99.58 | 99.53 | 99.14 | 96.74 | 94.45 | 77.71 | 46.81 |
| 5:1 | 99.68 | 99.56 | 99.6 | 96.06 | 91.18 | 59.13 | 25.95 |
| 0:1 | 99.65 | 99.23 | 98.26 | 75.05 | 46.66 | 6.37 | 1.30 |

TABLE 15

| CaCl$_2$:Tygacil® Molar ratio | Day 0 | Day 1 | Day 2 | Day 5 | Day 7 | Day 14 | Day 21 |
|---|---|---|---|---|---|---|---|
| 30:1 | 99.58 | 99.55 | 99.29 | 97.79 | 95.9 | 86.94 | 69.71 |
| 20:1 | 99.62 | 99.51 | 99.18 | 97.00 | 93.81 | 80.6 | 55.28 |
| 12:1 | 99.60 | 99.41 | 98.94 | 94.94 | 91.13 | 69.3 | 40.59 |
| 5:1 | 99.65 | 99.42 | 98.66 | 92.83 | 85.72 | 53.1 | 24.74 |
| 0:1 | 99.60 | 99.34 | 98.25 | 74.61 | 45.63 | 6.26 | 1.53 |

TABLE 16

| ZnCl$_2$:Tygacil® Molar ratio | Day 0 | Day 1 | Day 2 | Day 5 | Day 7 | Day 14 | Day 21 |
|---|---|---|---|---|---|---|---|
| 12:1 | 99.44 | 99.27 | 99.49 | 98.60 | 97.66 | 92.50 | 83.58 |
| 5:1 | 99.48 | — | 99.22 | 97.42 | 96.21 | 87.22 | 71.55 |
| 0:1 | 99.62 | — | 98.22 | 73.43 | 43.3 | 6.37 | 1.57 |

While Tigecycline decomposed in all tubes over 21 days, the rate of decomposition was significantly lower in solutions containing higher molar ratios of metal cation. The rates of Tigecycline decomposition in the presence of calcium or magnesium cations were similar, however, the rate of Tigecycline decomposition in the presence of zinc was significantly lower.

Example 4

Effect of pH on the Stability of Tygacil® Solutions Containing Metal Cations at 37° C.

A 10 mg/mL aqueous solution of Tygacil® (Lot D 90293, 53 mg) was prepared, and 1650 µL aliquots were dispensed into four 15 mL polypropylene tubes. The volume of each tube was adjusted to 5500 µL with various dilutions of 0.1 M MgCl$_2$, 0.1 M CaCl$_2$, or 0.1 M ZnCl$_2$, or water (control), to achieve the desired molar ratio of a 1:1 ratio of Tigecycline: metal cation. Sample solutions from each 15 ml tube were taken and adjusted to pH 4, 5, or 6 with 0.1 N or 1 N solutions of NaOH or HCl, taking care to minimize volume changes. Samples solutions were incubated in the dark at 37° C. Samples were taken at various time points and analyzed by HPLC. The fraction of remaining Tigecycline (expressed as a percentage of the starting concentration) in each sample was determined.

The percentages of Tigecycline remaining at Day 0, 1, 2, 5, 7, and 14 for solutions of Tygacil® at 1:1 ratios with $MgCl_2$, $CaCl_2$, or $ZnCl_2$ at various pHs are shown in TABLE 17, TABLE 18, and TABLE 19, respectively. TABLE 20 shows percentages of Tigecycline remaining at Day 0, 1, 2, 5, 7, and 14 for solutions of Tygacil® only at various pHs

TABLE 17

| pH for 1:1 $MgCl_2$:Tygacil® | Day 0 | Day 1 | Day 2 | Day 5 | Day 7 | Day 14 |
|---|---|---|---|---|---|---|
| pH 4 | 99.51 | 98.89 | 98.89 | 95.72 | 90.92 | 54.54 |
| pH 5 | 99.55 | 99.09 | 98.00 | 84.77 | 63.60 | 15.89 |
| pH 6 | 99.53 | 98.36 | 95.79 | 44.81 | 23.71 | 5.19 |

TABLE 18

| pH for 1:1 $CaCl_2$:Tygacil® | Day 0 | Day 1 | Day 2 | Day 5 | Day 7 | Day 14 |
|---|---|---|---|---|---|---|
| pH 4 | 99.49 | 98.88 | 98.84 | 94.43 | 90.06 | 55.91 |
| pH 5 | 99.66 | 99.02 | 97.8 | 81.96 | 69.23 | 28.89 |
| pH 6 | 99.62 | 98.70 | 97.87 | 92.45 | 87.40 | 56.79 |

TABLE 19

| pH for 1:1 $ZnCl_2$: Tygacil® | Day 0 | Day 1 | Day 2 | Day 5 | Day 7 | Day 14 |
|---|---|---|---|---|---|---|
| pH 4 | 99.47 | 98.62 | 99.03 | 96.14 | 93.15 | 73.25 |
| pH 5 | 99.6 | 99.21 | 98.96 | 93.02 | 83.48 | 39.93 |
| pH 6 | 99.54 | 99.3 | 99.16 | 94.58 | 86.35 | 49.21 |

TABLE 20

| pH for Tygacil® | Day 0 | Day 1 | Day 2 | Day 5 | Day 7 | Day 14 |
|---|---|---|---|---|---|---|
| pH 4 | 99.48 | 99.07 | 98.93 | 94.28 | 87.05 | 44.75 |
| pH 5 | 99.6 | 98.94 | 96.89 | 49.21 | 27.49 | 2.16 |
| pH 6 | 99.47 | 95.27 | 59.56 | 10.74 | 2.4 | 5.22 |

While Tigecycline decomposed in all tubes over 14 days, the rate of decomposition was significantly lower in solutions with a pH lower than pH 6. The rates of Tigecycline decomposition in the presence of calcium or magnesium cations were similar at pH 4 and 5; however, the rate of Tigecycline decomposition in the presence of magnesium at pH 6 was significantly greater. The rate of Tigecycline decomposition at pH 4 and 5 in solutions containing zinc was lower than solutions containing magnesium or calcium. The rates of Tigecycline decomposition at pH 6, in solutions containing zinc or calcium were similar. The rate of Tigecycline decomposition at all pHs was much lower in the presence of metal cations, especially at higher pH.

Example 5

Effect of pH on the Stability of Tygacil® Solutions Containing High Concentrations of Metal Cations at 37° C.

A 10 mg/mL aqueous solution of Tygacil® (Lot D 90293, 53 mg) was prepared, and 1650 µL aliquots were dispensed into four 15 mL polypropylene tubes. The volume of each tube was adjusted to 5500 µL with various dilutions of 1 M $MgCl_2$, 1 M $CaCl_2$, or 1 M $ZnCl_2$, or water (control), to achieve the desired molar ratio of a 1:12 ratio of Tigecycline: metal cation. Sample solutions from each 15 ml tube were taken and adjusted to pH 4, 5, or 6 with 0.1 N or 1 N solutions of NaOH or HCl, taking care to minimize volume changes. Samples solutions were incubated in the dark at 37° C. Samples were taken at various time points and analyzed by HPLC. The fraction of remaining Tigecycline in each sample was determined.

The percentages of Tigecycline remaining at Day 0, 1, 2, 5, 7, and 14 for solutions of Tygacil® at 1:12 ratios with $MgCl_2$, $CaCl_2$, or $ZnCl_2$ at various pHs are shown in TABLE 21, TABLE 22, and TABLE 23, respectively.

TABLE 21

| pH for 12:1 $MgCl_2$: Tygacil® | Day 0 | Day 1 | Day 2 | Day 5 | Day 7 | Day 14 |
|---|---|---|---|---|---|---|
| pH 4 | 99.47 | 98.62 | 99.18 | 97.49 | 95.72 | 83.14 |
| pH 5 | 99.61 | 98.87 | 99.12 | 96.53 | 93.72 | 69.08 |
| pH 6 | 99.58 | 99.26 | 99.21 | 95.6 | 96.96 | 85.86 |

TABLE 22

| pH for 12:1 $CaCl_2$: Tygacil® | Day 0 | Day 1 | Day 2 | Day 5 | Day 7 | Day 14 |
|---|---|---|---|---|---|---|
| pH 4 | 99.48 | 97.24 | 98.89 | 96.01 | 92.85 | 73.05 |
| pH 5 | 99.74 | 99.36 | 99.41 | 97.64 | 95.94 | 89 |
| pH 6 | 99.61 | 99.44 | 99.48 | 98 | 97.09 | 92.18 |

TABLE 23

| pH for 12:1 $ZnCl_2$: Tygacil® | Day 0 | Day 1 | Day 2 | Day 5 | Day 7 | Day 14 |
|---|---|---|---|---|---|---|
| pH 4 | 99.49 | 99.29 | 99.36 | 98.73 | 98.35 | 95.19 |
| pH 5 | 99.56 | 99.47 | 99.47 | 98.38 | 98.04 | 93.38 |
| pH 6 | 99.65 | 99.38 | 99.49 | 98.78 | 98.79 | 97.67 |

While tigecycline decomposed in all tubes over 14 days, the rate of decomposition was slower in solutions at pH 6. The rates of Tigecycline decomposition in the presence of calcium were slower in solutions at greater pH. When formulated as Tygacil, the rates of tigecycline decomposition in the presence of zinc or magnesium were faster at pH 5.

Example 6

Effect of pH on the Stability of Minocycline Solutions Containing High Concentrations of $MgCl_2$ at 37° C.

A 10 mg/mL Minocycline hydrochloride aqueous solution was prepared, and 2500 µL aliquots were dispensed into two 15 mL polypropylene tubes. The volume of each tube was adjusted to 5500 µL with either a dilution of 1 M MgCl$_2$ to achieve a molar ratio of a 1:10 ratio of Minocycline:metal cation, or water. Sample solutions from each 15 ml tube were taken and adjusted to pH 4, 5, or 6 with 0.1 N or 1 N solutions of NaOH or HCl, taking care to minimize volume changes. Sample solutions were incubated in the dark at 37° C. Samples were taken at various time points and analyzed by HPLC. The fraction of minocycline remaining in each sample was determined.

The percentages of Minocycline remaining at Day 0, 1, 2, 5, 7, and 14 for solutions at various pHs of Minocycline at 1:10 ratio with MgCl$_2$, or Minocycline solutions alone are shown in TABLE 24, and TABLE 25, respectively.

TABLE 24

| pH for 10:1 MgCl$_2$: Minocycline | Day 0 | Day 1 | Day 2 | Day 5 | Day 7 | Day 14 |
|---|---|---|---|---|---|---|
| pH 4 | 98.63 | 96.97 | 96.46 | 94.76 | 93.43 | 84.32 |
| pH 5 | 98.69 | 97.05 | 96.19 | 93.01 | 89.31 | 75.42 |
| pH 6 | 99.03 | 97.1 | 96.04 | 88.45 | 83.88 | 76.25 |

TABLE 25

| pH for Minocycline alone | Day 0 | Day 1 | Day 2 | Day 5 | Day 7 | Day 14 |
|---|---|---|---|---|---|---|
| pH 4 | 98.75 | 96.37 | 96.21 | 94.99 | 92.78 | 81.82 |
| pH 5 | 98.41 | 96.72 | 95.29 | 85.01 | 75.14 | 35.43 |
| pH 6 | 98.19 | 95.47 | 87.55 | 39.17 | 14.56 | 2.2 |

While Minocycline decomposed in all tubes over 14 days, the rate of decomposition was significantly lower in solutions containing magnesium, especially at higher pH.

Example 7

Stability of Tigecycline Solutions Containing Mixtures of CaCl$_2$ and MgCl$_2$ at pH 6 and 37° C.

A 10 mg/mL aqueous solution of Tigecycline was prepared, and 450 pt aliquots were dispensed into 15 mL polypropylene tubes. The volume of each tube was adjusted to 1500 µL with various dilutions of 1 M MgCl$_2$ and 1 M CaCl$_2$, or water (control), to achieve the desired molar ratios of Tigecycline:metal cation. Sample solutions from each 15 ml tube were taken and adjusted to pH 6 with 0.1 N or 1 N solutions of NaOH or HCl, taking care to minimize volume changes. Samples solutions were incubated in the dark at 37° C. Samples were taken at various time points and analyzed by HPLC. The fraction of Tigecycline remaining in each sample was determined.

The percentages of Tigecycline remaining at Day 0, 1, 2, 5, 7, 14, and 21 for solutions of at various ratios of Tigecycline: MgCl$_2$: CaCl$_2$ at pH 6 are shown in TABLE 26.

TABLE 26

| MgCl$_2$:CaCl$_2$: tigecycline Molar ratio | Day 0 | Day 1 | Day 2 | Day 5 | Day 7 | Day 14 | Day 21 |
|---|---|---|---|---|---|---|---|
| 5:5:1 | 98.25 | 98.77 | 98.23 | 96.91 | 92.13 | 83.64 | 65.21 |
| 5:10:1 | 98.37 | 98.23 | 98.59 | 97.76 | 96.10 | 89.74 | 79.83 |
| 10:5:1 | 98.17 | 98.21 | 98.46 | 96.59 | 93.90 | 80.00 | 59.39 |
| 10:10:1 | 98.32 | 98.24 | 98.50 | 97.38 | 95.62 | 87.14 | 72.88 |
| 5:0:1 | 98.18 | 97.93 | 97.53 | 90.58 | 76.71 | 40.42 | 12.54 |
| 10:0:1 | 98.16 | 98.00 | 98.23 | 94.91 | 89.12 | 62.54 | 35.75 |
| 15:0:1 | 98.25 | 98.13 | 98.21 | 96.23 | 92.32 | 72.15 | 48.75 |
| 20:0:1 | 98.2 | 98.08 | 98.28 | 96.46 | 93.72 | 78.66 | 57.66 |
| 0:5:1 | 98.11 | 98.15 | 98.28 | 97.19 | 95.68 | 89.2 | 77.2 |
| 0:10:1 | 98.12 | 98.2 | 98.55 | 97.1 | 96.53 | 91.74 | 84.69 |
| 0:15:1 | 98.15 | 98.21 | 98.59 | 97.5 | 96.93 | 92.71 | 86.37 |
| 0:20:1 | 98.28 | 98.63 | 98.57 | 97.4 | 97.35 | 93.09 | 87.45 |
| 0:0:1 | 97.91 | 88.97 | 60.59 | 16.36 | 7.33 | 4.14 | 0 |

While Tigecycline decomposed in all tubes over 21 days, the rate of decomposition was significantly lower in solutions containing greater relative amounts of calcium cations.

Example 8

Effects of MgCl$_2$ on Minocyline-Induced Hemolysis in an In Vitro Model of Venous Phlebitis In vitro hemolysis of rabbit red blood cells (RBCs) after exposure to minocycline formulated in MgCl$_2$ or CaCl$_2$ was compared to in vitro hemolysis of RBCs after exposure to minocycline in saline, or exposure to amphotericin B. Minocycline HCl (LKT laboratories) stock solutions were prepared with MgCl$_2$ in saline, saline, or lactated ringer, and the pH was adjusted with NaOH. Rabbit and sheep red blood cells (RBCs) were obtained from Innovative Research laboratory (Michigan, USA). Immediately before use, RBCs were washed three times in 0.9% saline and adjusted to a density of 5% in saline. 200 µl RBCs was added to 800 µl minocycline solution, and mixed by gentle inversion for 2-5 seconds. Samples were incubated at 37° C. or 30 minutes or at 25° C. for 2-5 minutes. Incubated samples were centrifuged at 12000×g for 4 minutes and the supernatants were removed and the hemoglobin absorbance was read at 540 nm. Samples were tested in triplicate. Amphotericin B (MP Biomedicals) and distilled H$_2$O, or Triton-x and distilled H$_2$O were used as positive controls; saline was used as a negative control. Percent hemolysis was calculated according to the following formula:

$$\text{Percent hemolysis} = \frac{(\text{absorbance of sample}) - (\text{absorbance of blank})}{\text{Absorbance of Distilled H}_2\text{O}} \times 100$$

In a set of experiments, the pH of minocycline solutions formulated with divalent cations was adjusted to pH 5.85. For RBCs incubated in a minocycline saline solution, hemolysis was in the range of 44%-84% (FIG. 1). For RBCs incubated in a minocycline with Mg$^{2+}$ or Ca$^{2+}$, hemolysis was approximately 2%. Results summarizing the percent in vitro hemolysis of rabbit RBCs incubated with different formulations of minocycline or amphoterin B at 25° C. are summarized in Table 27.

TABLE 27

| Solution | Hemolysis of RBCs in solution relative to water (%) |
|---|---|
| 5 mg/ml minocycline, 10 equiv Mg, pH 5.85 | 2.8 |
| 2.5 mg/ml minocycline, 10 equiv Mg, pH 5.85 | 3.2 |
| 0.5 mg/ml minocycline, 10 equiv Mg, pH 5.85 | 2.3 |
| 5 mg/ml minocycline, 5 equiv Ca, pH 5.85 | 2.2 |
| 2.5 mg/ml minocycline, 5 equiv Ca, pH 5.85 | 2.94 |
| 0.5 mg/ml minocycline, 5 equiv Ca, pH 5.85 | 2.20 |
| 5 mg/ml minocycline, saline, pH 4.17 | 81.64 |
| 2.5 mg/ml minocycline, saline, pH 4.17 | 84.37 |
| 0.5 mg/ml minocycline, saline, pH 4.17 | 43.82 |
| Amphoterin B | 101.31 |

Figure 2:
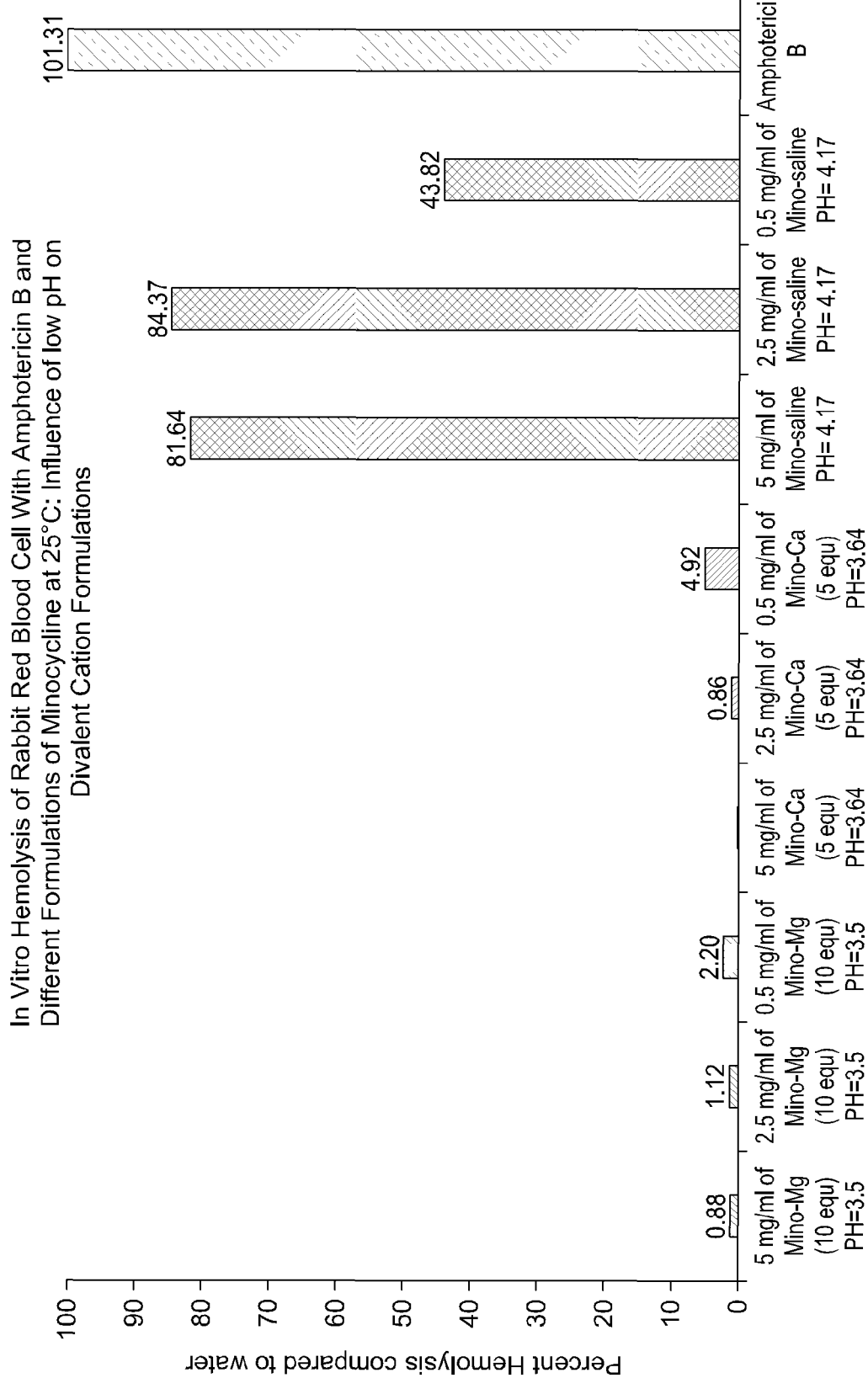
FIG. 2 shows a graph of percent hemolysis of rabbit red blood cells incubated with various concentrations of minocycline in various solutions relative to hemolysis in water.

In another set of experiments, the pH of a minocycline solution formulated with divalent cations was not adjusted and was allowed to fall below the pH of minocycline in saline. For RBCs incubated in a minocycline saline solution, hemolysis was in the range of 44%-84% (FIG. 2). For RBCs incubated in a minocycline with $Mg^{2+}$ or $Ca^{2+}$, hemolysis was in the range of 0%-5%. Results summarizing the percent in vitro hemolysis of rabbit RBCs incubated with different formulations of minocycline at low pH, or amphoterin B at 25° C. are summarized in Table 28.

TABLE 28

| Solution | Hemolysis of RBCs in solution relative to water (%) |
|---|---|
| 5 mg/ml minocycline, 10 equiv Mg, pH 3.5 | 0.88 |
| 2.5 mg/ml minocycline, 10 equiv Mg, pH 3.5 | 1.12 |
| 0.5 mg/ml minocycline, 10 equiv Mg, pH 3.5 | 2.20 |
| 5 mg/ml minocycline, 5 equiv Ca, pH 3.64 | — |
| 2.5 mg/ml minocycline, 5 equiv Ca, pH 3.64 | 0.86 |
| 0.5 mg/ml minocycline, 5 equiv Ca, pH 3.64 | 4.92 |
| 5 mg/ml minocycline, saline, pH 4.17 | 81.64 |
| 2.5 mg/ml minocycline, saline, pH 4.17 | 84.37 |
| 0.5 mg/ml minocycline, saline, pH 4.17 | 43.82 |
| Amphoterin B | 101.31 |

Hemolysis of RBCs was reduced in an in vitro model of venous phlebitis with minocycline solutions formulated with divalent cations compared to minocycline solutions formulated without divalent cations.

In another set of experiments, hemolysis of rabbit RBCs was measured after exposure to 2.5 mg/ml minocycline formulated with different rations of divalent cations ($MgCl_2$, $MgSO_4$, or $CaCl_2$). Hemolysis was compared to Minocycline HCl; Triton-x and $H_2O$ were used as positive controls. Results are summarized in Table 29 and shown in FIGS. 4-6.

TABLE 29

| 2.5 mg/ml minocycline solution | | Hemolysis of RBCs |
|---|---|---|
| Cation | Molar ratio cation:minocycline | in solution relative to water (%) |
| $MgSO_4$ | 1:2 | 22.52 |
| | 1:1 | 24.59 |
| | 2:1 | 40.87 |
| | 3:1 | 25.67 |
| | 5:1 | 2.86 |
| | 7:1 | 1.96 |
| | 10:1 | 0.19 |
| $MgCl_2$ | 1:2 | 46.91 |
| | 1:1 | 63.77 |
| | 2:1 | 74.87 |
| | 3:1 | 64.62 |
| | 5:1 | 9.43 |
| | 7:1 | 1.57 |
| | 10:1 | 0.35 |
| $CaCl_2$ | 1:2 | 75.22 |
| | 1:1 | 83.89 |
| | 2:1 | 50.84 |
| | 3:1 | 26.58 |
| | 5:1 | 1.16 |
| | 7:1 | 0.75 |
| | 10:1 | 0.40 |
| Minocycline only | | 37.44 |
| Triton-x | | 97.82 |

Figure 3:
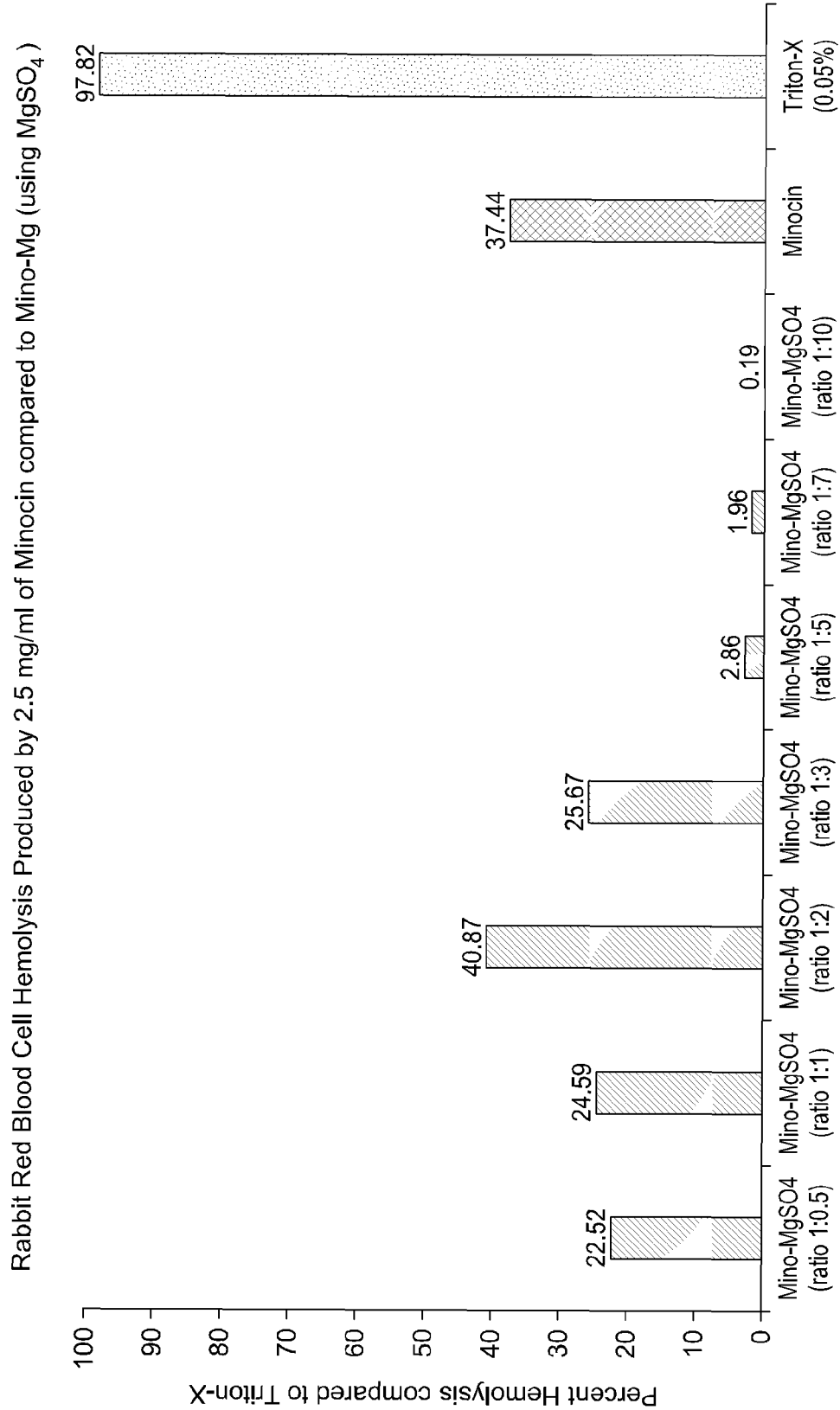
FIG. 3 depicts a graph of rabbit RBC hemolysis caused by minocycline formulated in different ratios of $MgSO_4$.
Figure 4:
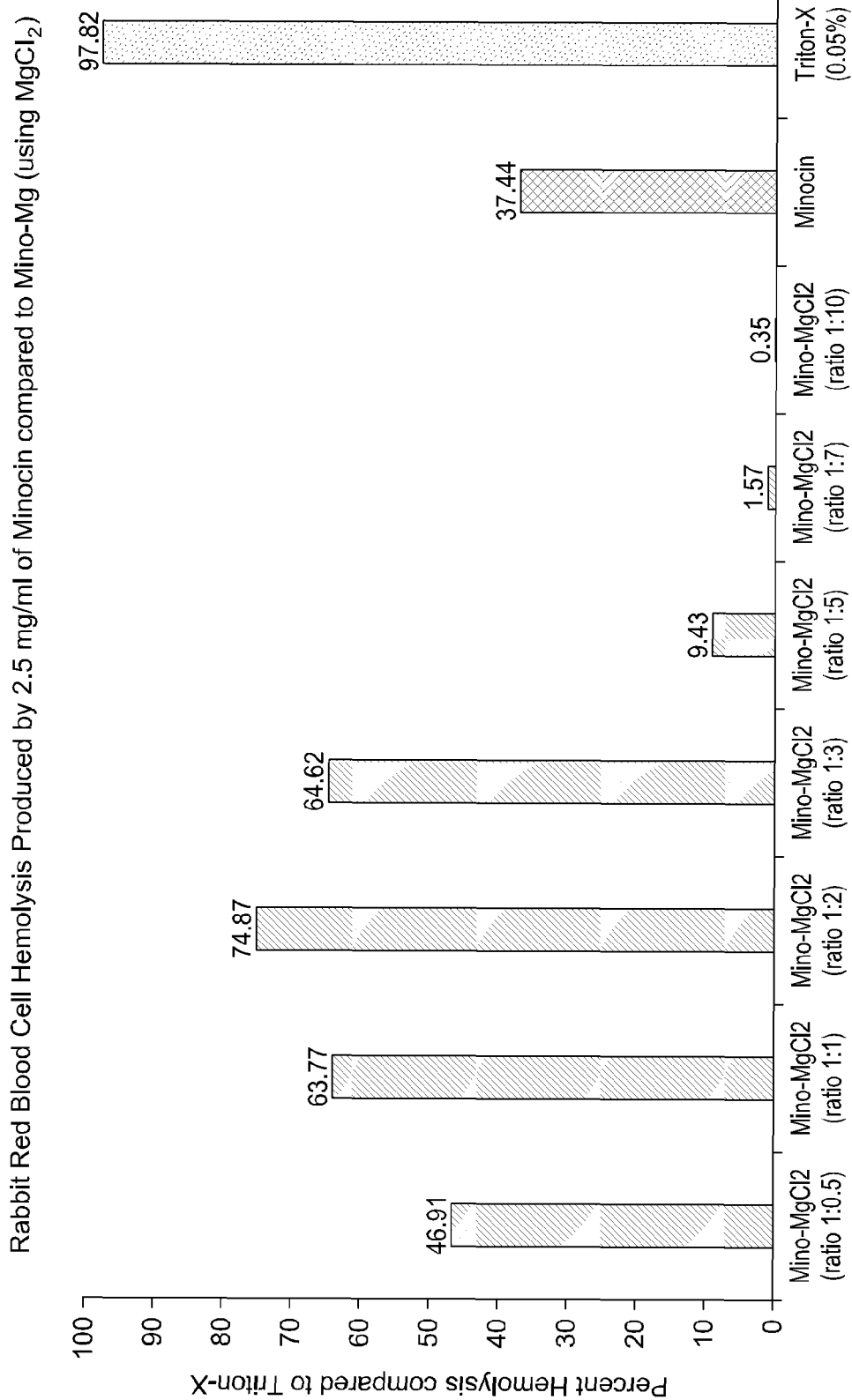
FIG. 4 depicts a graph of rabbit RBC hemolysis caused by minocycline formulated in different ratios of $MgCl_2$.
Figure 5:
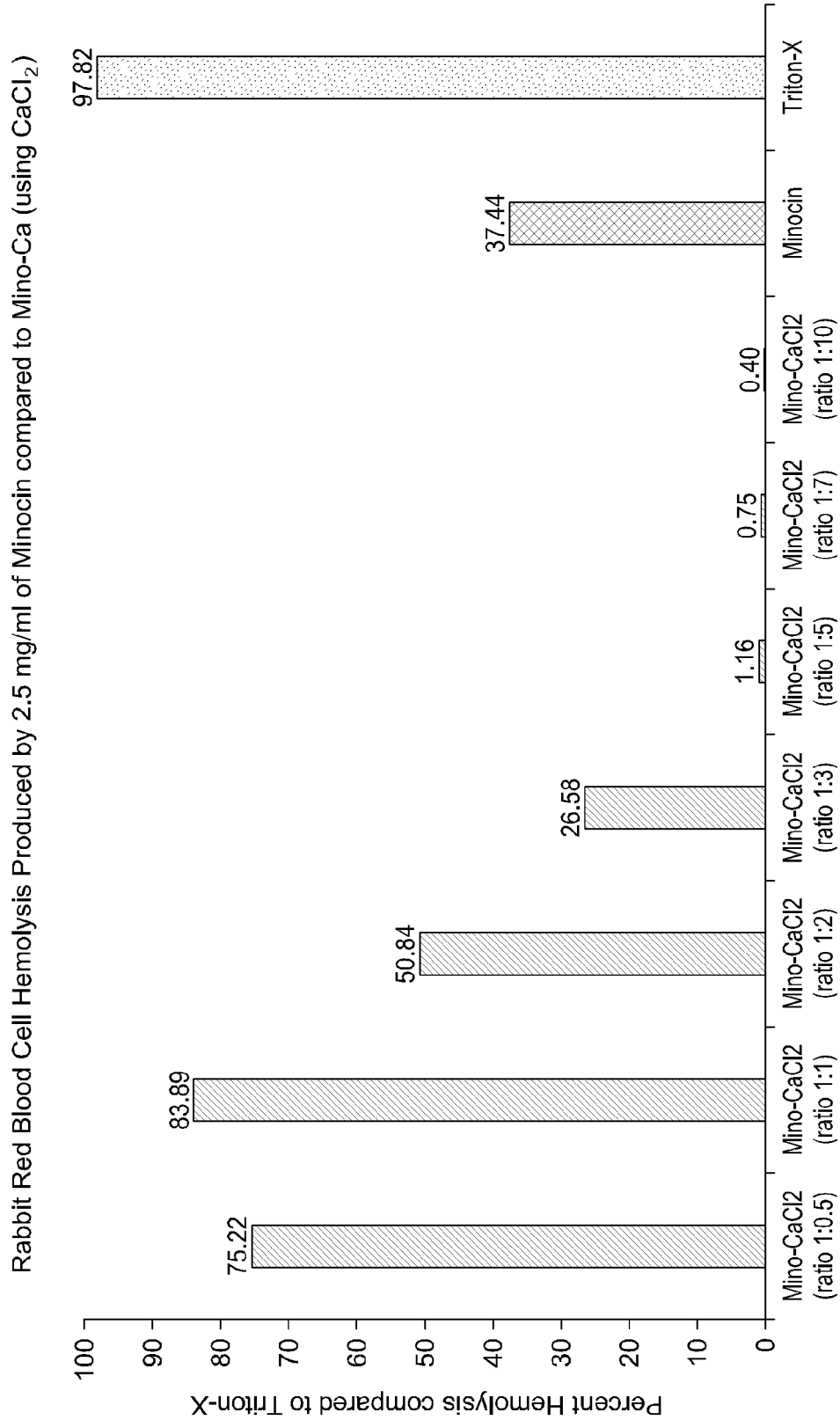
FIG. 5 depicts a graph of rabbit RBC hemolysis caused by minocycline formulated in different ratios of $CaCl_2$.

FIG. 3 and FIG. 4 show the degree of rabbit RBC hemolysis produced by minocycline formulated in different ratios of $MgSO_4$ or $MgCl_2$, respectively, compared to Minocycline only. The data indicates that a 5:1 molar ratio of magnesium to minocycline or greater inhibits the RBC hemolysis observed with minocycline alone. Minocycline (minocin) produced a relative RBC hemolysis of 37%. FIG. 5 shows the degree of rabbit RBC hemolysis produced by minocycline formulated in different ratios of $CaCl_2$. This data shows that a 5:1 molar ratio of calcium to minocycline inhibits the RBC hemolysis observed with minocycline HCl alone.

Overall, these data all suggest that high molar ratios (e.g., a 5:1 molar ratio or greater) of divalent cation ($Mg^{+2}$ or $Ca^{+2}$) to minocycline results in significant inhibition of rabbit RBC hemolysis observed with minocycline HCl.

Example 9

Solubility of Minocycline with Divalent Cations

Mixtures were prepared containing minocycline and divalent cations ($Mg^{2+}$ or $Ca^{2+}$) at varying stoichiometry and pH. The solubility of minocycline was assessed according to the turbidity of the mixture at 0 hr, 24 hr, 48 hr, 72 hr, 96 hr, 120 hr, 144 hr, and 168 hr. A clear solution denoted complete solubility. Table 30 summarizes data for minocycline with $Mg^{2+}$ at 0 hr and 24 hr. Table 31 summarizes data for minocycline with $Ca^{2+}$ at 0 hr and 24 hr.

TABLE 30

| | | \multicolumn{16}{c|}{Molar ratio cation (Mg$^{2+}$):Minocycline} |
|---|---|---|---|---|---|---|---|---|---|---|---|---|---|---|---|---|---|
| | | 0 | | 1:2 | | 1:1 | | 2:1 | | 3:1 | | 5:1 | | 7:1 | | 10:1 | |
| Time (hr) | | 0 | 24 | 0 | 24 | 0 | 24 | 0 | 24 | 0 | 24 | 0 | 24 | 0 | 24 | 0 | 24 |
| 1 mg/ml minocycline | pH 4 | o | o | | | | | | | | | o | o | o | o | o | o |
| | pH 5 | o | o | | | | | | | | | o | o | o | o | o | o |
| | pH 6 | o | o | | | | | | | | | o | o | o | o | o | o |
| | pH 7 | o | o | | | | | | | | | o | o | o | o | o | o |
| 5 mg/ml minocycline | pH 4 | o | o | o | o | o | o | o | o | o | o | o | o | o | o | o | o |
| | pH 5 | o | o | o | o | o | o | o | o | o | o | o | o | o | o | o | o |
| | pH 6 | o | o | • | • | • | • | • | • | • | • | o | • | o | • | o | o |
| 10 mg/ml minocycline | pH 4 | o | o | o | o | o | o | o | o | o | o | o | o | o | o | o | o |
| | pH 5 | o | o | o | o | o | • | o | • | o | • | o | o | o | o | o | o |
| | pH 6 | o | o | • | • | • | • | • | • | • | • | • | • | • | • | • | • |
| 20 mg/ml minocycline | pH 4 | o | • | | | | | | | | | o | o | o | o | o | o |
| | pH 5 | o | • | | | | | | | | | o | • | o | • | o | • |
| 30 mg/ml minocycline | pH 4 | o | • | | | | | | | | | o | o | o | o | o | o |
| | pH 5 | o | • | | | | | | | | | o | • | o | • | o | • |

•: insoluble;
o: soluble

TABLE 31

| | | \multicolumn{16}{c|}{Molar ratio cation (Ca$^{2+}$):minocycline} |
|---|---|---|---|---|---|---|---|---|---|---|---|---|---|---|---|---|---|
| | | 0 | | 1:2 | | 1:1 | | 2:1 | | 3:1 | | 5:1 | | 7:1 | | 10:1 | |
| Time (hr) | | 0 | 24 | 0 | 24 | 0 | 24 | 0 | 24 | 0 | 24 | 0 | 24 | 0 | 24 | 0 | 24 |
| 1 mg/ml minocycline | pH 4 | o | o | | | | | | | | | o | o | o | o | o | o |
| | pH 5 | o | o | | | | | | | | | o | o | o | o | o | o |
| | pH 6 | o | o | | | | | | | | | o | o | o | o | o | o |
| | pH 7 | o | o | | | | | | | | | o | • | o | • | o | • |
| 5 mg/ml minocycline | pH 4 | o | o | o | o | o | o | o | o | o | o | o | o | o | o | o | o |
| | pH 5 | o | o | o | o | o | o | o | o | o | o | o | o | o | o | o | o |
| | pH 6 | o | o | • | o | o | o | o | o | o | o | o | o | o | o | o | o |
| 10 mg/ml minocycline | pH 4 | o | o | o | o | o | o | | | | | | | | | | |
| | pH 5 | o | o | o | o | o | o | | | | | | | | | | |
| | pH 6 | o | o | o | o | o | o | | | | | | | | | | |
| 20 mg/ml minocycline | pH 4 | o | • | | | | | | | | | o | o | o | o | o | o |
| | pH 5 | o | o | | | | | | | | | o | o | o | o | o | o |
| 30 mg/ml minocycline | pH 4 | o | • | | | | | | | | | o | • | o | • | o | • |
| | pH 5 | o | • | | | | | | | | | o | o | o | o | o | o |

•: insoluble;
o: soluble

The data demonstrates that minocycline stays in solution upon introduction of a cation at concentrations of 10 mg/ml and less if the pH is less than 5. At higher pH, introduction of a cation initially reduces solubility. For example, a 5 mg/ml minocycline solution at pH 6 becomes insoluble on addition of Mg$^{2+}$. Surprisingly, at a molar ratio of cation:minocycline of 5:1 or more, the minocycline of such solutions becomes soluble, suggesting that high ratios of cation increases the solubility of minocycline.

Table 32 summarizes data for minocycline with Mg$^{2+}$ at 48 hr and 72 hr.

TABLE 32

| | | \multicolumn{16}{c|}{Molar ratio cation (Mg$^{2+}$):minocycline} |
|---|---|---|---|---|---|---|---|---|---|---|---|---|---|---|---|---|---|
| | | 0 | | 1:2 | | 1:1 | | 2:1 | | 3:1 | | 5:1 | | 7:1 | | 10:1 | |
| Time (hr) | | 48 | 72 | 48 | 72 | 48 | 72 | 48 | 72 | 48 | 72 | 48 | 72 | 48 | 72 | 48 | 72 |
| 1 mg/ml minocycline | pH 4 | o | o | | | | | | | | | o | o | o | o | o | o |
| | pH 5 | o | o | | | | | | | | | o | o | o | o | o | o |
| | pH 6 | o | o | | | | | | | | | o | o | o | o | o | o |
| | pH 7 | o | o | | | | | | | | | o | o | o | o | o | o |
| 5 mg/ml minocycline | pH 4 | o | o | o | o | o | o | o | o | o | o | o | o | o | o | o | o |
| | pH 5 | o | o | o | • | o | o | o | o | o | o | o | o | o | o | o | o |
| | pH 6 | o | o | • | • | • | • | • | • | • | • | • | • | • | • | • | • |
| 10 mg/ml minocycline | pH 4 | • | o | o | o | o | o | o | o | o | o | o | o | o | o | o | o |
| | pH 5 | • | • | o | • | • | • | • | • | • | • | o | • | o | • | o | • |
| | pHm 6 | • | • | • | • | • | • | • | • | • | • | • | • | • | • | • | • |

TABLE 32-continued

| | | Molar ratio cation ($Mg^{2+}$):minocycline | | | | | | | | | | | | | | |
|---|---|---|---|---|---|---|---|---|---|---|---|---|---|---|---|---|
| | | 0 | | 1:2 | | 1:1 | | 2:1 | | 3:1 | | 5:1 | | 7:1 | | 10:1 | |
| Time (hr) | | 48 | 72 | 48 | 72 | 48 | 72 | 48 | 72 | 48 | 72 | 48 | 72 | 48 | 72 | 48 | 72 |
| 20 mg/ml minocycline | pH 4 | • | • | | | | | | | | | ○ | ○ | ○ | ○ | ○ | ○ |
| | pH 5 | • | • | | | | | | | | | • | • | • | • | • | • |
| 30 mg/ml minocycline | pH 4 | • | • | | | | | | | | | ○ | ○ | ○ | ○ | ○ | ○ |
| | pH 5 | • | • | | | | | | | | | • | • | • | • | • | • |

•: insoluble;
○: soluble

Example 10

Long-Term Stability of Tigecycline at Various Temperatures

Table 33, Table 34, and Table 35 show percentage remaining tigecycline for different formulations of tigecycline at pH 6, stored at 37° C., room temperature, and 4° C., respectively. Formulations of tigecycline comprising increasing concentrations of tigecycline and increasing concentrations of $CaCl_2$ showed increased stability.

TABLE 33

| Salt | Formulation stored at 37° C. | Stability of tigecycline (%) | | | | | |
|---|---|---|---|---|---|---|---|
| | | 0 day | 1 day | 2 days | 5 days | 7 days | 14 days |
| $MgCl_2$ | 12 eq 20 mg/mL | 97.97 | 97.43 | 96.37 | 92.63 | 88.41 | |
| | 5 eq 20 mg/mL | 98.09 | 97.38 | 96.42 | 88.64 | 81.62 | |
| | 2 eq 20 mg/mL | 97.95 | 97.28 | 94.1 | 80.59 | 69.88 | |
| | 12 eq 3 mg/mL | 98.17 | 98.05 | 97.08 | 93.78 | 88.16 | |
| | 5 eq 3 mg/mL | 98.3 | 97.72 | 96.77 | 86.97 | 73.76 | |
| | 2 eq 3 mg/mL | 98.21 | 97.22 | 93.75 | 62.21 | 45.31 | |
| $CaCl_2$ | 12 eq 20 mg/mL | 98.3 | 98 | 97.63 | 96.1 | 95.24 | 91.44 |
| | 5 eq 20 mg/mL | 98.16 | 97.75 | 97.4 | 95.82 | 94.81 | 89.26 |
| | 2 eq 20 mg/mL | 98.25 | 97.85 | 97.22 | 95.28 | 93.64 | 88.61 |
| | 12 eq 3 mg/mL | 98.29 | 98.03 | 97.74 | 96.79 | 95.92 | 91.07 |
| | 5 eq 3 mg/mL | 98.21 | 97.96 | 97.32 | 95.37 | 94.42 | 86.36 |
| | 2 eq 3 mg/mL | 98.17 | 97.74 | 96.57 | 92.99 | 90.22 | |
| $ZnCl_2$ | 1 eq 20 mg/mL | 98.26 | 97.19 | 93.86 | 81.02 | 72.41 | |
| | 1 eq 3 mg/mL | 98.29 | 97.88 | 96.73 | 86.5 | 74.32 | |

TABLE 34

| Salt | Formulation stored at room temperature | Stability of tigecycline (%) | | | | | |
|---|---|---|---|---|---|---|---|
| | | 0 day | 7 days | 14 days | 28 days | 42 days | 58 days |
| $MgCl_2$ | 12 eq 20 mg/mL | 97.97 | 96.56 | 93.4 | 79.44 | | |
| | 5 eq 20 mg/mL | 98.09 | 94.2 | 82.17 | | | |
| | 2 eq 20 mg/mL | 97.95 | 87.57 | 67.91 | | | |
| | 12 eq 3 mg/mL | 98.17 | 97.22 | 94.91 | 80.14 | | |
| | 5 eq 3 mg/mL | 98.3 | 96.45 | 89.91 | | | |
| | 2 eq 3 mg/mL | 98.21 | 92.66 | 66.91 | | | |
| $CaCl_2$ | 12 eq 20 mg/mL | 98.3 | 97.91 | 97.36 | 95.69 | 95.32 | 93.02 |
| | 5 eq 20 mg/mL | 98.16 | 97.88 | 97.23 | 95.24 | 94.08 | 90.78 |
| | 2 eq 20 mg/mL | 98.25 | 97.97 | 97.08 | 94.42 | 93.08 | 87.95 |
| | 12 eq 3 mg/mL | 98.29 | 98.01 | 97.7 | 96.37 | 95.78 | 93.67 |
| | 5 eq 3 mg/mL | 98.21 | 97.84 | 97.29 | 95.39 | 94.22 | 90.37 |
| | 2 eq 3 mg/mL | 98.17 | 97.53 | 96.47 | 92.85 | 90.07 | 79.52 |
| $ZnCl_2$ | 1 eq 20 mg/mL | 98.26 | 82.44 | 65.73 | | | |
| | 1 eq 3 mg/mL | 98.29 | 97.11 | 93.1 | | | |

TABLE 35

| Salt | Formulation stored at 4° C. | Stability of tigecycline (%) | | | | | |
|---|---|---|---|---|---|---|---|
| | | 0 day | 14 day | 28 days | 35 days | 58 days | 162 days |
| $MgCl_2$ | 12 eq 20 mg/mL | 97.97 | 97.68 | 96.16 | 95.36 | 89.95 | |
| | 5 eq 20 mg/mL | 98.09 | 96.22 | 78.05 | 69.76 | | |
| | 2 eq 20 mg/mL | 97.95 | 91.23 | 54.38 | 43.33 | | |
| | 12 eq 3 mg/mL | 98.17 | 97.76 | 95.76 | 94.19 | 80.31 | |
| | 5 eq 3 mg/mL | 98.3 | 97.48 | 91.75 | 86.21 | | |
| | 2 eq 3 mg/mL | 98.21 | 96.23 | 84.6 | 76.81 | | |

TABLE 35-continued

| Salt | Formulation stored at 4° C. | Stability of tigecycline (%) | | | | | |
|---|---|---|---|---|---|---|---|
| | | 0 day | 14 day | 28 days | 35 days | 58 days | 162 days |
| CaCl$_2$ | 12 eq 20 mg/mL | 98.3 | 98.28 | 97.78 | 97.61 | 97.87 | 96.4 |
| | 5 eq 20 mg/mL | 98.16 | 97.97 | 97.65 | 97.79 | 97.78 | 95.22 |
| | 2 eq 20 mg/mL | 98.25 | 98.08 | 97.69 | 97.8 | 97.75 | 94.9 |
| | 12 eq 3 mg/mL | 98.29 | 98.37 | 98.16 | 97.79 | 98.15 | 97.27 |
| | 5 eq 3 mg/mL | 98.21 | 98.17 | 97.97 | 97.76 | 97.99 | 96.75 |
| | 2 eq 3 mg/mL | 98.17 | 98.14 | 97.45 | 97.53 | 97.56 | 93.35 |
| ZnCl$_2$ | 1 eq 20 mg/mL | 98.26 | 77.12 | 53.06 | 45.63 | | |
| | 1 eq 3 mg/mL | 98.29 | 97.73 | 96.38 | 95.02 | 88.53 | |

Example 11

Solubility of Tetracycline Formulations

The solubility of four non-dimethlyamino tetracyclines, with and without Mg$^{2+}$, was examined. The results are summarized in Table 36.

TABLE 36

| | | Molar ratio cation (Mg$^{2+}$):antibiotic | | | | | | | |
|---|---|---|---|---|---|---|---|---|---|
| | | 0 | 0.5:1 | 1:1 | 2:1 | 3:1 | 5:1 | 7:1 | 10:1 |
| 10 mg/ml tetracycline | pH 4 | • | • | • | • | • | • | • | • |
| | pH 5 | • | • | • | • | • | • | • | • |
| | pH 6 | • | • | • | • | • | • | • | • |
| 10 mg/ml chlortetracycline | pH 4 | • | | | | | o | o | o |
| | pH 5 | • | | | | | • | • | • |
| | pH 6 | • | | | | | • | • | • |
| 10 mg/ml doxycycline | pH 4 | o | | | | | • | • | • |
| | pH 5 | o | | | | | • | • | • |
| | pH 6 | | | | | | o# | o# | o# |
| 10 mg/ml oxytetracycline | pH 4 | • | | | | | • | • | • |
| | pH 5 | • | | | | | • | o | o |
| | pH 5 | • | | | | | • | o | o |

•: insoluble;
o: soluble;
fell out of solution after 24 hrs at room temperature A comparison with the results for minocycline described in Example 9 indicates that non-dimethylamino-tetracylines, such as tetracycline, chlortetracycline, doxycycline, and oxytetracycline have solubility characteristics that differ from dimethylamino-tetracylines. For example, as summarized in Table 36, tetracycline remains insoluble at various pH and amounts of a divalent cation such as Mg$^{2+}$. Chlortetracycline becomes soluble with increasing concentrations of a divalent cation, but remains insoluble in the absence of any divalent cation, such as Mg$^{2+}$. Doxycycline is soluble in the absence of divalent cations, such as Mg$^{2+}$, but is insoluble in the presence of divalent cations at low pH. Similarly, oxytetracycline remains insoluble in the presence of divalent cations, such as Mg$^{2+}$, at low pH.

Example 12

Study of the Effect of Mg$^{2+}$ on the Uptake of Minocycline in Human Umbilical Vein Endothelial Cells (HUVEC)

Cells and reagents: Human umbilical vein endothelial cells (HUVEC) were purchased from Lonza and maintained according to manufacturer's recommendations in EGM-2 media. A 10 mg/mL solution of minocycline was prepared in 13.6 mg/mL Na-acetate without addition of Mg. This stock solution was further diluted in saline to 1 mg/mL with addition of Mg in the form of 1 M MgSO$_4$ to generate the following molar ratios of Mg to minocycline: 0, 1, 2.5, 5, 10, 25.

Uptake experimental conditions: HUVECs were seeded at 4.5×10$^5$ cells/well density in 6-well plates in EGM-2 media. Two days after seeding, cells were washed once with 2 mL of saline, and then 2 mL of 1 mg/mL drug solution in saline prepared as described above was placed in each well in triplicate. Plates were incubated in a CO$_2$ incubator at 37° C. for 30 min. Drug solutions were aspirated and cells were washed once with 2 mL of saline. 0.5 mL of saline was placed in each well and the cell monolayer was scraped using a plastic cell scraper. Cell suspensions were transferred to 1.5 mL plastic tubes and sonicated for 30 sec at maximal power. Cell lysates were spun down for 10 min on a table top microcentrifuge at maximum speed and supernatants were collected. Several wells of HUVEC cells were treated with saline only and processed the same way as drug-treated cells to generate mock cell lysate which was used below for calibration curve preparation.

Sample preparation for LCMS analysis: To prepare a calibration curve, 1 mg/mL minocycline solution in water was diluted in mock cell lysate to produce 100 µl of standards with the following concentrations: 10, 5, 2, 1, 0.5, 0.2, 0.1, 0.05, 0.02, 0.01 µg/ml.

50 µl of supernatants from drug-treated samples or standards were mixed with 200 µl of 1% trifluoroacetic acid in acetonitrile containing 1 µg/mL of gatifloxacin, vortexed and centrifuged at 3000 g for 30 min at RT. 150 µl of supernatants was removed and mixed with 450 µl of water. After vortexing, the mixture was centrifuged at 3000 g for 5 min at RT. Supernatants were collected and subjected to LCMS analysis to determine minocycline concentration.

Data processing: Uptake data were presented as percentage relative to the sample with no Mg present, which was considered as 100%.

Figure 6:
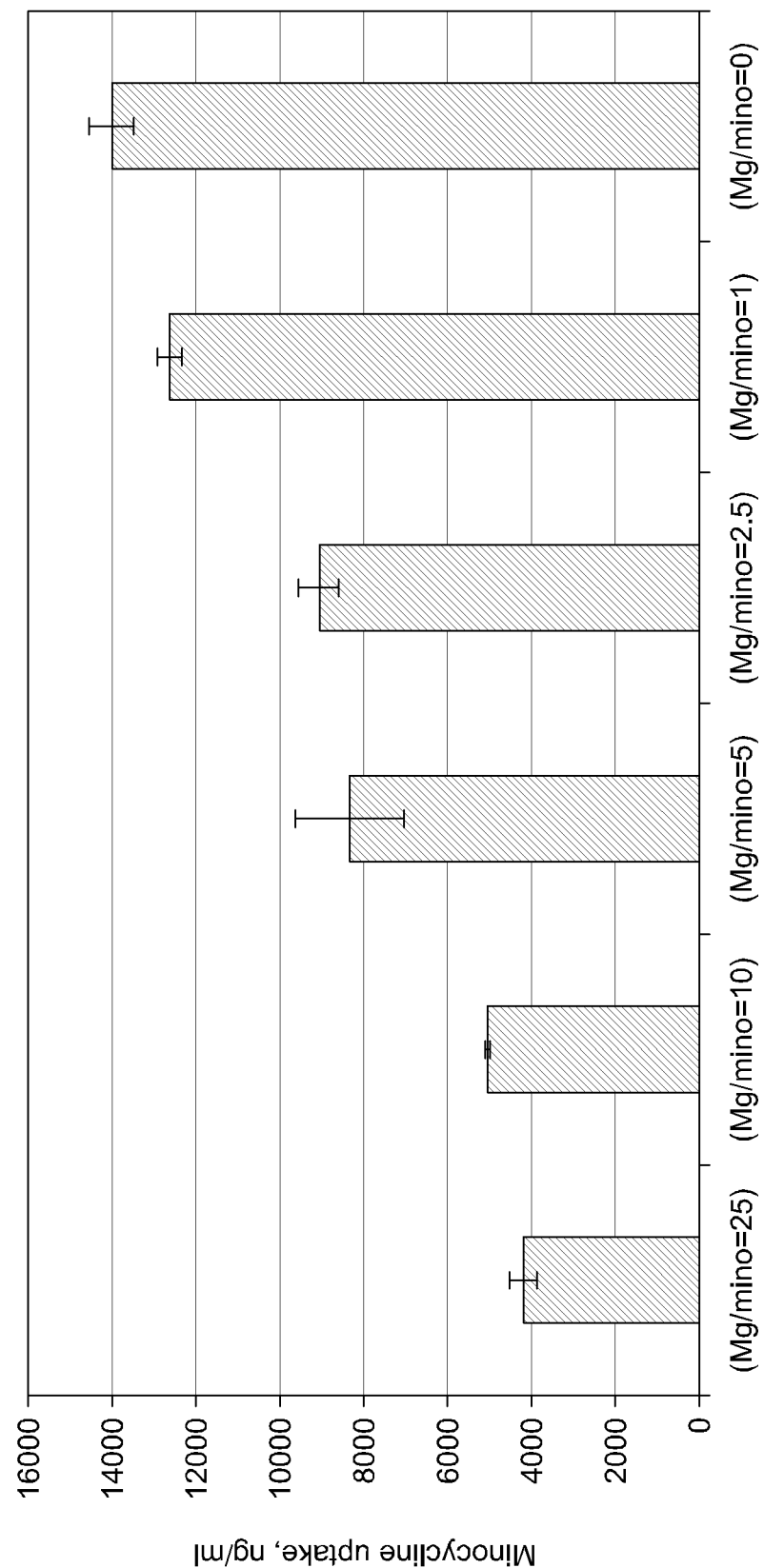
FIG. 6 depicts a graph for minocycline uptake by HVEC at various concentrations of divalent cation.
Figure 7:
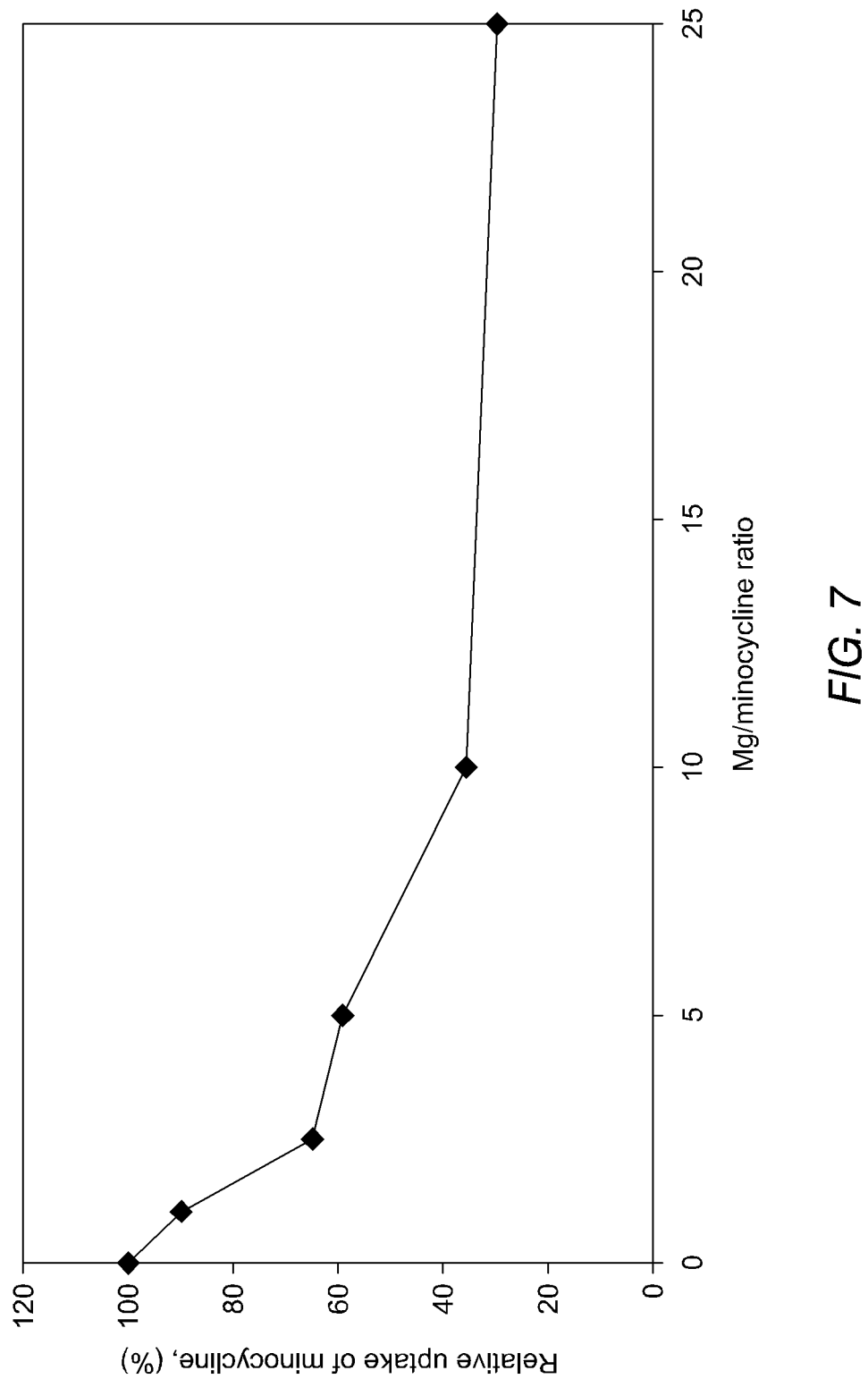
FIG. 7 depicts a graph for minocycline uptake by HVEC at various concentrations of divalent cation.

Uptake of minocycline at 1 mg/mL in saline with various Mg/minocycline ratios was tested in HUVEC with an incubation time was 30 min. The results are summarized in FIG. 6 and FIG. 7. FIGS. 6 and 7 demonstrate that a decrease in intracellular uptake of minocycline is observed as the concentration of a divalent cation, such as Mg$^{2+}$ increases. While not being bound by any particular theory, this result suggests that the mechanism for the reduction in hemolysis observed in the minocycline/cation formulations described herein may be attributed to reduced RBC updake.

Example 13

Preparing Certain Formulations of Dimethylamino-Tetracylines

Formulation 1

A formulation comprising minocycline with MgCl$_2$ and NaOH suitable for intravenous administration is prepared.

100 mg minocycline is added to a 10 ml aqueous solution of $MgCl_2.6H_2O$ to provide a cation to minocycline molar ratio of 5:1 and a 10 mg/ml minocycline solution. The pH of the mixture is adjusted by adding NaOH to a pH in the range of pH 4.5-pH 5.5. A single attempt of lyophilization resulted in a non-flocculent solid.

Formulation 2

A formulation comprising minocycline with $MgSO_4$ and sodium acetate suitable for intravenous administration is prepared. 100 mg minocycline is added to an aqueous solution of $MgSO_4.7H_2O$ to provide a cation to minocycline molar ratio of 5:1 and a 10 mg/ml minocycline solution. The pH of the solution is adjusted by adding sodium acetate to a pH in the range of pH 4.5-pH 5.5. The solution is then lyophilized to dryness. Reconstitution of the lyophile in 10 ml water results in a solution having a pH in the range of pH 4.5-pH 5.5 and an osmolality in the range of 275 mOsm/kg-375 mOsm/kg.

Formulation 3

A formulation comprising minocycline with $Mg(C_2H_3O_2)_2$ suitable for intravenous administration is prepared. 100 mg minocycline is added to an aqueous solution of $Mg(C_2H_3O_2)_2.3H_2O$ to provide a cation to minocycline molar ratio of 5:1 and a 10 mg/ml minocycline solution. The solution is then lyophilized to dryness.

Formulation 4

A formulation comprising minocycline with $MgSO_4$ and NaOH suitable for intravenous administration is prepared. 100 mg minocycline is added to an aqueous solution of $MgSO_4.7H_2O$ to provide a cation to minocycline molar ratio of 5:1 and a 10 mg/ml minocycline solution. The pH of the solution is adjusted by adding NaOH to a pH in the range of pH 4.5-pH 5.5. The solution is lyophilized to dryness. Reconstitution of the lyophile in 10 ml water results in a solution having a pH in the range of pH 4.5-pH 5.5 and an osmolality in the range of 150 mOsm/kg-250 mOsm/kg.

Formulation 5

A formulation comprising tigecycline with $MgSO_4$ and NaOH suitable for intravenous administration is prepared. 50 mg tigecycline is added to 10 ml aqueous solution of $MgSO_4.7H_2O$ to provide a cation to tigecycline molar ratio of 5:1. The pH of the solution is adjusted by adding NaOH to a pH in the range of pH 5.5-pH 6.5. The solution is then lyophilized to dryness. Reconstitution of the lyophile in 10 ml water results in a solution having a pH in the range of pH 5.5-pH 6.5.

Formulation 6

A formulation comprising tigecycline with $MgSO_4$ and NaOH suitable for intravenous administration is prepared. 50 mg tigecycline is added to 10 ml aqueous solution of $MgSO_4.7H_2O$ to provide a cation to tigecycline molar ratio of 12:1. The pH of the solution is adjusted by adding NaOH to a pH in the range of pH 5.5-pH 6.5. The solution is then lyophilized to dryness. Reconstitution of the lyophile in 10 ml water results in a solution having a pH in the range of pH 5.5-pH 6.5.

Formulation 7

A formulation comprising tigecycline with $MgCl_2$ and NaOH suitable for intravenous administration is prepared. 50 mg tigecycline is added to 10 ml aqueous solution of $MgCl_2.6H_2O$ to provide a cation to tigecycline molar ratio of 5:1. The pH of the solution is adjusted by adding NaOH to a pH in the range of pH 5.5-pH 6.5. The solution is then lyophilized to dryness. Reconstitution of the lyophile in 10 ml water results in a solution having a pH in the range of pH 5.5-pH 6.5.

Formulation 8

A formulation comprising tigecycline with $MgCl_2$ and NaOH suitable for intravenous administration is prepared. 50 mg tigecycline is added to 10 ml aqueous solution of $MgCl_2.6H_2O$ to provide a cation to tigecycline molar ratio of 12:1. The pH of the solution is adjusted by adding NaOH to a pH in the range of pH 5.5-pH 6.5. The solution is then lyophilized to dryness. Reconstitution of the lyophile in 10 ml water results in a solution having a pH in the range of pH 5.5-pH 6.5.

Formulation 9

A formulation comprising tigecycline with $MgSO_4$ and NaOH suitable for topical administration is prepared. 50 mg tigecycline is added to 10 ml aqueous solution of $MgSO_4.7H_2O$ to provide a cation to tigecycline molar ratio of 5:1. The pH of the solution is adjusted by adding NaOH to a pH in the range of pH 6.0-pH 7.0. The solution is then lyophilized to dryness. Reconstitution of the lyophile in 10 ml water results in a solution having a pH in the range of pH 6.0-pH 7.0.

Formulation 10

A formulation comprising tigecycline with $MgSO_4$ and NaOH suitable for topical administration is prepared. 50 mg tigecycline is added to 10 ml aqueous solution of $MgSO_4.7H_2O$ to provide a cation to tigecycline molar ratio of 12:1. The pH of the solution is adjusted by adding NaOH to a pH in the range of pH 6.0-pH 7.0. The solution is then lyophilized to dryness. Reconstitution of the lyophile in 10 ml water results in a solution having a pH in the range of pH 6.0-pH 7.0.

Formulation 11

A formulation comprising tigecycline with $CaCl_2$ and NaOH suitable for topical administration is prepared. 50 mg tigecycline is added to 10 ml aqueous solution of $CaCl_2.6H_2O$ to provide a cation to tigecycline molar ratio of 5:1. The pH of the solution is adjusted by adding NaOH to a pH in the range of pH 6.0-pH 7.0. The solution is then lyophilized to dryness. Reconstitution of the lyophile in 10 ml water results in a solution having a pH in the range of pH 6.0-pH 7.0.

Formulation 12

A formulation comprising tigecycline with $CaCl_2$ and NaOH suitable for topical administration is prepared. 50 mg tigecycline is added to 10 ml aqueous solution of $CaCl_2.6H_2O$ to provide a cation to tigecycline molar ratio of 12:1. The pH of the solution is adjusted by adding NaOH to a pH in the range of pH 6.0-pH 7.0. The solution is then lyophilized to dryness. Reconstitution of the lyophile in 10 ml water results in a solution having a pH in the range of pH 6.0-pH 7.0.

Example 14

Minocycline Kits

Kit 1

A kit is prepared comprising two vials. The first vial is prepared by dissolving 108 mg minocycline HCl in an acidic solution. The solution is lyophilized to dryness. The second vial contains 10 ml diluent that includes 26.9 mg/ml $MgSO_4.7H_2O$ and 13.6 mg/mL $Na(C_2H_3O_2)_2.3H_2O$. The lyophile is then reconstituted with the diluent prior to use.

Kit 2

A kit is prepared comprising two vials. The first vial is prepared by dissolving 108 mg minocycline HCl in an acidic solution. The solution is lyophilized to dryness. The second vial contains 10 ml diluent that includes 26.9 mg/ml MgSO$_4$.7H$_2$O and enough NaOH to adjust the pH to approximately 5. The lyophile is then reconstituted with the diluent prior to use.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material. The term "comprising" as used herein is synonymous with "including," "containing," or "characterized by," and is inclusive or open-ended and does not exclude additional, unrecited elements or method steps. All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A method of treating a bacterial infection, comprising administering a therapeutically effective amount of a pharmaceutical composition to a subject in need thereof via topical administration to the eye of the subject, the pharmaceutical composition comprising an aqueous solution of tigecycline and a divalent or trivalent metal cation, wherein the pH of the solution is greater than 4 and less than 7 and the molar ratio of divalent or trivalent metal cation to tigecycline is greater than 6:1.

2. The method of claim 1, wherein the molar ratio of divalent or trivalent metal cation to tigecycline is greater than 8:1.

3. The method of claim 1, wherein the molar ratio of divalent or trivalent metal cation to tigecycline is greater than 10:1.

4. The method of claim 1, wherein the molar ratio of divalent or trivalent metal cation to tigecycline is about 12:1.

5. The method of claim 1, wherein the divalent or trivalent metal cation is a divalent metal cation.

6. The method of claim 1, wherein the divalent or trivalent metal cation is calcium.

7. The method of claim 1, wherein the solution comprises calcium chloride or calcium sulfate.

8. The method of claim 1, wherein the divalent or trivalent metal cation is magnesium.

9. The method of claim 1, wherein the solution comprises magnesium sulfate or magnesium chloride.

10. The method of claim 1, wherein the concentration of tigecycline is at least 1 mg/ml.

11. The method of claim 1, wherein the concentration of tigecycline is 5 mg/ml.

12. The method of claim 1, wherein the solution comprises one or more additional constituents selected from the group consisting of hydrocortisone, dexamethasone, thonzonium bromide, tyloxapol, boric acid, and benzalkonium chloride.

13. The method of claim 1, wherein the solution does not comprise a component selected from the group consisting of an antioxidant, a pyridine-containing compound, gluconate, an alcohol, glycerol, polyethylene glycol, a pyrrolidone-containing compound, a water-miscible local anaesthetic, urea, lactose, and a dehydrating agent.

14. The method of claim 1, wherein the pharmaceutical composition is contained within a vial prior to administration.

15. The method of claim 14, wherein the vial is a single-use vial.

16. A method of treating a bacterial infection, comprising:
reconstituting a water-soluble solid composition in a pharmaceutically acceptable diluent to form a solution; and
administering a therapeutically effective amount of the solution to a subject in need thereof via topical administration to the eye of the subject,
wherein the water-soluble solid composition comprises tigecycline and a divalent or trivalent metal cation, wherein the molar ratio of divalent or trivalent metal cation to tigecycline is greater than 6:1.

17. The method of claim 16, wherein the molar ratio of divalent or trivalent metal cation to tigecycline is greater than 8:1.

18. The method of claim 16, wherein the molar ratio of divalent or trivalent metal cation to tigecycline is greater than 10:1.

19. The method of claim 16, wherein the molar ratio of divalent or trivalent metal cation to tigecycline is about 12:1.

20. The method of claim 16, wherein the divalent or trivalent metal cation is a divalent metal cation.

21. The method of claim 16, wherein the divalent or trivalent metal cation is calcium.

22. The method of claim 16 comprising calcium chloride or calcium sulfate.

23. The method of claim 16, wherein the divalent or trivalent metal cation is magnesium.

24. The method of claim 16 comprising magnesium sulfate or magnesium chloride.

25. The method of claim 16, wherein the water-soluble solid composition is in the form of a lyophile.

26. The method of claim 16, wherein the water-soluble solid composition is contained within a vial.

27. The method of claim 26, wherein the vial is a single-use vial.

28. The method of claim 26, wherein the vial comprises greater than 30 mg and less than 100 mg of tigecycline.

29. The method of claim 26, wherein the vial comprises at least 50 mg of tigecycline.

30. The method of claim 26, wherein the vial comprises at least 200 µg of tigecycline.

31. The method of claim 26, wherein the vial comprises at least 1 mg of tigecycline.

32. The method of claim 16, wherein the pharmaceutically acceptable diluent is water.

* * * * *